US008093012B2

(12) United States Patent
Hamann et al.

(10) Patent No.: US 8,093,012 B2
(45) Date of Patent: Jan. 10, 2012

(54) MULTIPLEX IN SITU IMMUNOHISTOCHEMICAL ANALYSIS

(75) Inventors: Stefan Hamann, Yonkers, NY (US); Michael Donovan, Cambridge, MA (US); Mark Clayton, Pawling, NY (US); Angeliki Kotsianti, New York, NY (US)

(73) Assignee: Aureon Laboratories, Inc., Yonkers, NY (US)

( * ) Notice: Subject to any disclaimer, the term of this patent is extended or adjusted under 35 U.S.C. 154(b) by 550 days.

(21) Appl. No.: 11/581,043

(22) Filed: Oct. 13, 2006

(65) Prior Publication Data

US 2007/0154958 A1 Jul. 5, 2007

Related U.S. Application Data

(60) Provisional application No. 60/726,809, filed on Oct. 13, 2005, provisional application No. 60/729,567, filed on Oct. 24, 2005, provisional application No. 60/817,824, filed on Jun. 30, 2006, provisional application No. 60/833,670, filed on Jul. 26, 2006.

(51) Int. Cl.
*G01N 33/533* (2006.01)
*G01N 33/543* (2006.01)
*G01N 33/563* (2006.01)
*G01N 33/567* (2006.01)
*G01N 33/574* (2006.01)
*G01N 33/577* (2006.01)
*C07K 16/18* (2006.01)

(52) U.S. Cl. ........ 435/7.23; 435/7.1; 435/7.2; 435/7.21; 435/7.24; 435/7.4; 435/7.8; 435/7.95; 435/40.5; 435/40.52; 435/960; 435/962; 436/503; 436/512; 436/518; 436/548; 436/64; 436/172; 436/175

(58) Field of Classification Search .................. 435/7.1, 435/7.2, 7.21, 7.23, 7.24, 7.4, 7.8, 7.95, 40.5, 435/40.52, 960, 962; 436/503, 512, 518, 436/548, 64, 172, 175

See application file for complete search history.

(56) References Cited

U.S. PATENT DOCUMENTS

| | | | | |
|---|---|---|---|---|
| 4,235,869 A | * | 11/1980 | Schwarzberg | 436/512 |
| 4,384,042 A | | 5/1983 | Miike et al. | 435/25 |
| 4,469,787 A | * | 9/1984 | Woods et al. | 435/7.4 |
| 4,520,110 A | | 5/1985 | Stryer et al. | 436/501 |
| 4,542,104 A | | 9/1985 | Stryer et al. | 436/536 |
| 4,603,209 A | | 7/1986 | Tsien et al. | 548/236 |
| 4,714,763 A | | 12/1987 | Theodoropulos | 544/31 |
| 4,774,339 A | | 9/1988 | Haugland et al. | 548/405 |
| 4,810,636 A | | 3/1989 | Corey | 435/14 |
| 4,812,409 A | | 3/1989 | Babb et al. | 435/7 |
| 4,849,362 A | | 7/1989 | DeMarinis et al. | 436/63 |
| 4,859,582 A | | 8/1989 | Stryer et al. | 435/5 |
| 4,945,171 A | | 7/1990 | Haugland et al. | 549/224 |
| 4,956,303 A | * | 9/1990 | Self | 436/542 |
| 4,981,977 A | | 1/1991 | Southwick et al. | 548/455 |
| 5,055,556 A | | 10/1991 | Stryer et al. | 530/370 |
| 5,132,432 A | | 7/1992 | Haugland et al. | 548/518 |
| 5,187,288 A | | 2/1993 | Kang et al. | 548/110 |
| 5,196,306 A | | 3/1993 | Bobrow et al. | 435/7.9 |
| 5,208,148 A | | 5/1993 | Haugland et al. | 435/14 |
| 5,227,487 A | | 7/1993 | Haugland et al. | 546/15 |
| 5,242,805 A | | 9/1993 | Naleway et al. | 435/18 |
| 5,248,782 A | | 9/1993 | Haugland et al. | 548/110 |
| 5,268,486 A | | 12/1993 | Woggoner et al. | 548/427 |
| 5,274,113 A | | 12/1993 | Kang et al. | 548/405 |
| 5,316,906 A | | 5/1994 | Haugland et al. | 435/4 |
| 5,362,628 A | | 11/1994 | Haugland et al. | 435/18 |
| 5,433,896 A | | 7/1995 | Kang et al. | 252/700 |
| 5,442,045 A | | 8/1995 | Haugland et al. | 530/391.3 |
| 5,443,986 A | | 8/1995 | Haughland et al. | 435/4 |
| 5,451,343 A | | 9/1995 | Neckers et al. | 252/582 |
| 5,459,276 A | | 10/1995 | Kuhn et al. | 548/159 |
| 5,486,616 A | | 1/1996 | Waggoner | 548/217 |
| 5,501,980 A | | 3/1996 | Katerinopoulos et al. | 436/74 |
| 5,569,587 A | | 10/1996 | Waggoner | 435/6 |
| 5,569,766 A | | 10/1996 | Waggoner et al. | 548/150 |
| 5,576,424 A | | 11/1996 | Mao et al. | 536/17.9 |
| 5,583,001 A | | 12/1996 | Bobrow et al. | 435/7.5 |
| 5,627,027 A | | 5/1997 | Waggoner | 435/6 |
| 5,696,157 A | | 12/1997 | Wang et al. | 514/457 |
| 5,731,158 A | | 3/1998 | Bobrow et al. | 435/7.5 |
| 5,773,236 A | | 6/1998 | Diwu et al. | 435/15 |
| 5,798,276 A | | 8/1998 | Haugland et al. | 436/546 |

(Continued)

FOREIGN PATENT DOCUMENTS

EP 1 065 250 A1 12/2004

(Continued)

OTHER PUBLICATIONS

Wessel et al., 1986. Two embryonic, tissue-specific molecules identified by a double-label immunofluorescence technique for monoclonal antibodies. J. Histochem. Cytochem. 34: 703-706.*

C. M. van der Loos, 1999. Immunoenzyme Multiple Staining Methods. Oxford: BIOS Scientific Publishers Limited.*

Ishikawa et al., 1983. Enzyme-labeling of anitbodies and their fragments for enzyme immunoassay and immunohistochemical staining. Journal of Immunoassay 4: 209-327.*

Kirkeby et al., 2005. Quantitative immunohistochemistry of fluorescence labelled probes using low-cost software. J. Immunological Meth. 301: 102-113.*

Baschong et al., 2001. Control of autofluorescence of archival formaldehyde-fixed, paraffin-embedded tissue in confocal laser scanning microscopy (CLSM). J. Histochem. Cytochem. 49: 1565-1571.*

(Continued)

*Primary Examiner* — Gail R Gabel
*Assistant Examiner* — James L Grun
(74) *Attorney, Agent, or Firm* — Mintz Levin Cohn Ferris Glovsky and Popeo, P.C.; Richard G. Gervase; Cynthia A. Kozakiewicz

(57) ABSTRACT

A method of in situ immunohistochemical analysis of a biological sample is provided. The method allows for the multiplex and simultaneous detection of multiple antigens, including multiple nuclear antigens, in a tissue sample.

39 Claims, 19 Drawing Sheets

U.S. PATENT DOCUMENTS

| | | | | |
|---|---|---|---|---|
| 5,808,044 | A | 9/1998 | Brush et al. | 536/25.32 |
| 5,830,912 | A | 11/1998 | Gee et al. | 514/457 |
| 5,846,737 | A | 12/1998 | Kang | 435/7.1 |
| 5,877,310 | A | 3/1999 | Reddington et al. | 536/25.32 |
| 6,002,003 | A | 12/1999 | Shen et al. | 544/232 |
| 6,004,536 | A | 12/1999 | Leung et al. | 424/9.6 |
| 6,008,373 | A | 12/1999 | Waggoner et al. | 548/427 |
| 6,043,025 | A | 3/2000 | Minden et al. | 435/4 |
| 6,127,134 | A | 10/2000 | Minden et al. | 435/7.2 |
| 6,130,094 | A | 10/2000 | Waggoner et al. | 436/63 |
| 6,130,101 | A | 10/2000 | Mao et al. | 436/546 |
| 6,133,445 | A | 10/2000 | Waggoner et al. | 546/36 |
| 6,162,931 | A | 12/2000 | Gee et al. | 549/223 |
| 6,229,055 | B1 | 5/2001 | Klaubert et al. | 568/765 |
| 6,252,053 | B1* | 6/2001 | Ohbayashi et al. | 530/391.3 |
| 6,339,392 | B1 | 1/2002 | Ashihara | 342/1 |
| 6,562,632 | B1 | 5/2003 | Szalecki et al. | 436/546 |
| 6,664,047 | B1 | 12/2003 | Haugland et al. | 435/6 |
| 6,716,979 | B2 | 4/2004 | Diwu et al. | 544/99 |
| 6,974,873 | B2 | 12/2005 | Leung et al. | 548/455 |
| 6,977,305 | B2 | 12/2005 | Leung et al. | 548/450 |
| 6,995,020 | B2 | 2/2006 | Capodieci et al. | 436/94 |
| 7,326,575 | B2 | 2/2008 | Capodieci et al. | 436/94 |
| 2003/0073149 | A1 | 4/2003 | Archer et al. | 435/7.92 |
| 2005/0262031 | A1 | 11/2005 | Saidi et al. | 706/21 |
| 2006/0199213 | A1 | 9/2006 | Capodieci et al. | 435/6 |

FOREIGN PATENT DOCUMENTS

| | | |
|---|---|---|
| WO | WO 97/40104 | 10/1997 |
| WO | WO 99/51702 | 10/1999 |
| WO | WO 01/21624 | 3/2001 |
| WO | WO 02/26891 | 4/2002 |
| WO | WO 03/030817 | 4/2003 |

OTHER PUBLICATIONS

Farr et al., 1981. Immunohistochemistry with enzyme labeled antibodies: a brief review. J. Immunolog. Meth. 47: 129-144.*

Ferri et al., 1997. Quadruple immunofluorescence: a direct visualization method. J. Histochem. Cytochem. 45: 155-158.*

Tsurui et al., 2000. Seven-color fluorescence imaging of tissue samples based on fourier spectroscopy and singular value decomposition. J. Histochem. Cytochem. 48: 653-662.*

Mason et al., 2000. Double immujnofluorescence labelling of routinely processed paraffin sections. Journal of Pathology 191: 452-461.*

Nakane, 1968. Simultaneous localization of multiple tissue antigens using the peroxidase-labeled antibody method: a study on pituitary glands of the rat. J. Histochem. Cytochem. 16: 557-560.*

Viegas et al., 2007. An improved and cost-effective methodology for the reduction of autofluorescence in direct immunofluorescence studies on formalin-fixed paraffin-embedded tissues. Eur. J. Histochem. 51: 59-66.*

Speel et al., 1995. Cytochemical detection systems for in situ hybridization, and the combination with immunocytochemistry. 'Who is still afraid of red, green, and blue?' Histochemical Journal 27: 833-858.*

Cromheeke et al., 1999. Inducible nitric oxide synthase colocalizes with signs of lipid oxidation/peroxidation in human atherosclerotic plaques. Cardiovascular Research 43: 744-754.*

Bauer et al., "Prognostic implications of ploidy and proliferative activity in diffuse large cell lymphomas", *Cancer Res.*, 46:3173-3178 (1986).

Bauer et al., "Prognostic implications of proliferative activity and DNA aneuploidy in colonic adenocarcinomas", *Lab. Invest.*, 57(3):329-335 (1987).

Beverloo, et al., "Immunochemical detection of proteins and nucleic acids on filters using small luminescent inorganic crystals as markers", *Anal. Biochem.*, 203(2):326-334 (1992).

Bird et al., "Single-chain antigen-binding proteins", *Science*, 242:423-426 (1988).

Braylan et al., "Percentage of cells in the S phase of the cell cycle in human lymphoma determined by flow cytometry: Correlation with labeling index and patient survival", *Cytometry*, 1(3):171-174 (1980).

Brinkley, M., "A brief survey of methods for preparing protein conjugates with dyes, haptens, and cross-linking reagents", *Bioconj. Chem.*, 3(1):2-13 (1992).

Brown et al., "Primary antibody-Fab fragment complexes: a flexible alternative to traditional direct and indirect immunolabeling techniques", *J. Histochem. Cytochem.*, 52(9):1219-1230 (2004).

Chan et al., "Method for multiplex cellular detection of mRNAs using quantum dot fluorescent in situ hybridization", *Nucl. Acids Res.*, 33(18)-e161:1-8 (2005).

Clark et al., "Predictions of relapse or survival in patients with node-negative breast cancer by DNA flow cytometry", *N. Eng. J. Med.*, 320(10):627-633 (1989).

Davies et al., "Antibody-Antigen Complexes", *Annu. Rev. Biochem.*, 59:439-473 (1990).

Haugland, R.P., Handbook of Fluorescent Probes and Research Chemicals, Sixth Edition, Chapters 1-3, pp. 7-80 (1996).

Huston et al., "Protein engineering of antibody binding sites: recovery of specific activity in an anti-digoxin single-chain Fv analogue produced in *Escherichia coli*", *Proc. Natl. Acad. Sci. USA*, 85:5879-5883 (1988).

Malmqvist, M., "Biospecific interaction analysis using biosensor technology", *Nature*, 361:186-187 (1993).

Ponder, B.AS.J., "Cell Marking Techniques and Their Application," in *Mammalian Development: A Practical Approach, Monk (ed.)*, Chapter 6, pp. 115-138 (1987).

Sigurdsson et al., "Indicators of prognosis in node-negative breast cancer", *N. Eng. J. Med.*, 322(15):1045-1053 (1990).

Silvestrini et al., "Cell kinetics as a prognostic marker in node-negative breast cancer", *Cancer*, 56(8):1982-1987 (1985).

Tuson et. al., "A novel immunohistochemical technique for demonstration of specific binding of human monoclonal antibodies to human cryostat tissue sections", *J. Histochem. Cytochem.*, 38(7):923-926 (1990).

Visscher et. al., "Prognostic significance of morphological parameters and flow cytometric DNA analysis in carcinoma of the breast", *Pathol. Annu.*, 25(part 1):171-210 (1990).

Ward et al., "Binding activities of a repertoire of single immunoglobulin variable domains secreted from *Escherichia coli*", *Nature*, 341:544-546 (1989).

Weinberg, D.S., "Proliferation indices in solid tumors", *Adv. Pathol. Lab. Med.*, 5:163-191 (1992).

Weinberg "Relative applicability of image analysis and flow cytometry in clinical medicine", in *Clinical Flow Cytometry: Principles and applications*, pp. 359-371 (1992).

Pileri, Stefano A., et al., "Antigen Retrieval Techniques in Immunohistochemistry: Comparison of Different Methods," *Journal of Pathology*, vol. 183, pp. 116-123 (1997).

Semar, Martin et al., "Quantitative Comparative Immunohistology," *Clinical Chemistry*, vol. 15 No. 6, pp. 505-508 (1969).

* cited by examiner

- Background
- Cytoplasm_AMACR_Neg
- Cytoplasm_AMACR_Pos
- Epit_AR_Neg_AMACR_Neg
- Epit_AR_Neg_AMACR_Pos
- Epit_AR_Pos_AMACR_Neg
- Epit_AR_Pos_AMACR_Pos
- Stroma_AR_Neg
- Stroma_AR_Pos
- unclassified

- Background
- Cytoplasm_AMACR_Neg
- Cytoplasm_AMACR_Pos
- Epit_AR_Neg_AMACR_Neg
- Epit_AR_Neg_AMACR_Pos
- Epit_AR_Pos_AMACR_Neg
- Epit_AR_Pos_AMACR_Pos
- Stroma_AR_Neg
- Stroma_AR_Pos
- unclassified

SEQUENCE LISTING

<160> NUMBER OF SEQ ID NOS: 3

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ser Thr Glu Asp Thr Ala Glu Tyr Ser Pro Phe Lys Gly Gly Tyr Thr
1               5                   10                  15

Lys

```
<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phospho-Tyr

<400> SEQUENCE: 2

Asn Phe Leu Met Asp Asn Ala Tyr Phe Cys Glu Ala Asp Ala Lys Lys
1               5                   10                  15

Lys

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Phe Tyr Gly Ala Thr Gly Glu Ser Tyr Asp Pro Thr Thr Lys Glu
1               5                   10                  15

Lys
```

MULTIPLEX IN SITU IMMUNOHISTOCHEMICAL ANALYSIS

RELATED APPLICATIONS

This application claims priority to U.S. Ser. No. 60/726,809, filed Oct. 13, 2005; U.S. Ser. No. 60/729,567, filed Oct. 24, 2005; U.S. Ser. No. 60/817,824, filed Jun. 30, 2006; and U.S. Ser. No. 60/833,670, filed Jul. 26, 2006 each of which is incorporated herein by reference in its entirety.

BACKGROUND

Immunofluorescence is a method to detect the distribution of an antigen in a biological sample through the specific binding of an antibody which itself is coupled to a fluorescent agent. The antibody binds specifically to the target molecule so that the fluorescent label qualitatively and/or quantitatively reports the presence of the target.

Different methods for the attachment of the fluorescent label have been developed. The direct labeling method utilizes a primary antibody (an antibody that recognizes the target) which is then coupled to the fluorescent agent. This method is labor-intensive and a certain amount of antibody might be inactivated in the process (if the label attaches itself to the antigen recognizing region of the antibody).

The indirect method utilizes a secondary antibody—an antibody which recognizes the primary antibody—coupled to a fluorescent agent to attach the label. Several different variations of this method have been described. Often the primary antibody is applied first to the sample, followed by a washing step and the application of a species specific secondary antibody which carries a fluorescent label. This often results in background problems due to unspecific binding of the secondary antibody to the tissue. Another approach has utilized preformed primary-secondary antibody complexes (Tuson et al. 1990). This method enables indirect labeling of primary antibodies derived from the same species, but the use of divalent secondary antibodies can lead to crosslinked complexes.

A similar approach which avoids this problem is the use of monovalent Fc specific Fab fragments for the generation of pre-formed complexes and has been commercialized by Molecular Probes (Zenon; Eugene, Oreg.). Others have modified this method by utilizing Fab fragments that recognize both the Fc and F(ab')$_2$ regions of the primary antibody (Brown et al. 2004). This approach is described in U.S. application Ser. No. 10/118,204 filed Apr. 5, 2002 which is incorporated herein by reference.

All the methods above have in common that the primary antibody is labeled before it is contacted with a biological sample. The primary antibody is either directly labeled with a fluorophore (through chemical means, by binding to secondary antibody or a Fab fragment labeled with a fluorescent agent) or that the primary antibodies are detected with a bivalent secondary antibody which is labeled with a fluorophore (usually by chemical means). This can cause problems especially in fixed, paraffin embedded tissue specimen which is generally less accessible to large molecules than other biological samples (e.g. fixed, permeabilized cultured cells). For example, an antibody in pre-formed complex with a secondary antibody has twice the molecular weight of the primary antibody. An antibody in a pre-formed complex with Fab fragments has about twice the molecular weight of the primary antibody if three Fab fragments are bound per antibody.

The increased size of these complexes can prevent sufficient penetration of the tissue and thus restrict or inhibit detection of the target molecule, cause excessive background staining and thus complicate the detection of the target molecule. This is especially relevant for the detection of a nuclear biomarker, where the antibody—Fab complexes are unable to penetrate the complexed protein of the nucleus and instead are found accumulated in the cytoplasm. Thus, a need exists for improved methods of analyzing intracellular antigens.

There is a growing body of evidence that tumor cell proliferation has prognostic significance for a variety of commonly occurring malignancies, including lymphoma (Braylan R. C., Diamond L. W., Powell M. L., Harty-Golder B. Percentage of cells in the S phase of the cell cycle in human lymphoma determined by flow cytometry: Correlation with labeling index and patient survival. Cytometry 1980; 1:171-174; and Bauer K. D., Merkel D. E., Winter J. N., et al. Prognostic implications of ploidy and proliferative activity in diffuse large cell lymphomas. Cancer Res 1986; 46:3173-3178), breast cancer (Clark G. M., Dressler L. G., Owens M. A., Pounds G., Oldaker T., McGuire W. L. Prediction of relapse or survival in patients with node-negative breast cancer by DNA flow cytometry. N Engl J Med 1989; 320:627-633; Silvestrini R., Daidone M. G., Gasparini G. Cell kinetics as a prognostic marker in node-negative breast cancer. Cancer 1985; 56:1982-1987; and Sigurdsson H., Baldetorp B., Borg A., et al. Indicators of prognosis in node-negative breast cancer. N Engl J Med 1990; 322:1045-1053), and colon cancer (Bauer K. D., Lincoln S. T., Vera-Roman J. M., et al. Prognostic implications of proliferative activity and DNA aneuploidy in colonic adenocarcinomas. Lab Invest 1987; 57:329-335). In some studies, tumor cell proliferation has independent prognostic significance, even if total DNA content analysis ("ploidy") does not (Visscher D. W., Zarbo R. J., Greenawald K. A., Crissman J. D. Prognostic significance of morphological parameters and flow cytometric DNA analysis in carcinoma of the breast. Pathol Ann 1990; 25(Part-I): 171-210).

Flow cytometry (FCM) has been used extensively to determine cell cycle activity, primarily by quantitation of the S-phase portion of the DNA content analysis ("ploidy"). This method suffers from a number of serious technical limitations, however. First, it may be difficult to obtain single cell suspensions from solid tumors, and variable numbers of tumor cells may be lost during preparation. Second, the tumor cells are variably diluted by benign normal and inflammatory cells, which can lead to underestimation of the S-phase fraction, particularly for DNA diploid tumors. Third, the complexity of the DNA content analysis ("ploidy"), which consists of a series of overlapping curves, may preclude the accurate use of curve-fitting algorithms to measure the S-phase portion of the histogram. Multicenter studies have shown poor reproducibility for flow-cytometric S-phase fraction, making the practical clinical usefulness of the measurement somewhat doubtful. Another problem associated with cell kinetic measurement by flow cytometry is that only the S-phase fraction is typically determined, whereas a significant proportion of the tumor cell population may reside in the $G_1$ phase of the cell cycle, comprised of cells committed to entering the cycle but not yet synthesizing DNA. Conceivably, two tumors may have identical S-phase fractions but differ significantly in the total fraction of cells in the nonresting state, and thus may exhibit different growth kinetics and response to cycle-dependent chemotherapeutic agents.

For all of these reasons, in situ methods of tumor cell cycle analysis may provide more biologically meaningful information than can be obtained using disaggregated tumor cells (Weinberg I. S. Relative applicability of image analysis and flow cytometry in clinical medicine. In: Bauer K. D., Duque R. E., eds. Flow cytometry: Principles and applications. Baltimore: Williams and Wllkins; 1992:359-372; and Weinberg D. S. Proliferation indices in solid tumors. Adv Pathol Lab Med 1992; 5:163-191). In addition to guaranteeing that the acquired measurements are made specifically on the tumor cells, in situ methods can allow more widespread sampling of the tumor and determination of tumor cell heterogeneity.

SUMMARY OF THE INVENTION

The present invention is based in part on the surprising discovery that combining a unique antigen retrieval technique and autoflourescene removal techniques of fluorescent in situ hybridization (FISH) allows for highly sensitive immunohistochemical detection of multiple target antigens in tissue samples. Accordingly, the invention describes a method for detecting target molecules in biological samples (e.g., formalin fixed, paraffin embedded tissue sections, tissue microarrays etc.).

The invention provides methods of detecting one or more targets in a biological sample. Two, three, four, five, six, seven, eight, nine, ten, fifteen or more targets are detected in a biological sample. Targets are detected by contacting a biological sample with a detection reagent and a labeling reagent under conditions in which the target, the detection reagent and the labeling reagent are capable of forming a complex. Detection reagent bound labeling reagent is then detected by the appropriate detection system (e.g., fluorescent microscope). The presence of the labeling reagent indicates the presence of the target in the biological sample. Similarly, the absence of the labeling reagent indicates the absence of the target in the biological sample. Additionally, the concentration of the target in the biological sample is determined by comparing the amount of labeling reagent detected with a control sample. Determination of the concentration of the target allows ratios of two or more targets in a sample to be determined. The ratio is related to a predetermined range to indicate a state of a disease. The control sample is for example a peptide microarray. In some aspects, detection of the target is indicative of tumor cell heterogeneity. Optionally, the biological sample is washed prior to and/or after addition of the detection reagent. The biological sample is contacted with the detection reagent and the labeling reagent sequentially. Alternatively, the biological sample is contacted with the detection reagent and the labeling reagent concurrently. When two or more targets are detected, optionally, a first detection reagent is allowed to complex with a first labeling reagent prior to contacting the biological sample.

The biological sample is for example a cell or tissue such as a paraffin-embedded tissue section or cryogenically preserved tissue section. The biological sample is immobilized on a surface. In some aspects the biological sample is substantially free of nucleic acids before detection of the labeling reagent.

The detection regent is for example an antibody or fragment thereof specific for the target of interest. The antibody is for example a monoclonal antibody. The target is a cell surface antigen, an intracellular antigen or a nuclear antigen. For example the target is an oncoprotein. Exemplary targets include an androgen receptor, a cytokeratin 18 protein, or a PTEN protein.

The labeling regent contains a detection reagent binding moiety and a detection moiety, i.e., label. An antibody binding moiety is for example a monovalent antibody fragment such as a Fab or Fab' fragment. The antibody-binding moiety is derived from a polyclonal or monoclonal antibody. The antibody binding fragment is an anti-Fc antibody fragment, an anti-kappa light chain antibody fragment, an anti-lambda light chain antibody fragment, or a single chain antibody fragment. Alternatively the antibody-binding moiety is a non-antibody protein such as protein G, a protein A, a protein L, and a lectin. The detection moiety is for example, a fluorescent moiety, a radioactive moiety, or an enzyme.

In some embodiments of the present invention, a platform for multiplexed quantitative antigen assessment is provided that combines immunofluorescence (IF) detection (e.g., using any of the methods described herein) with computer-assisted image analysis. Computer-generated measurements reflecting the presence, intensity, and distribution of fluorescent labels in tissue images are subject to supervised mathematical approaches in order to generate models, for example, for diagnosis and prognosis of disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
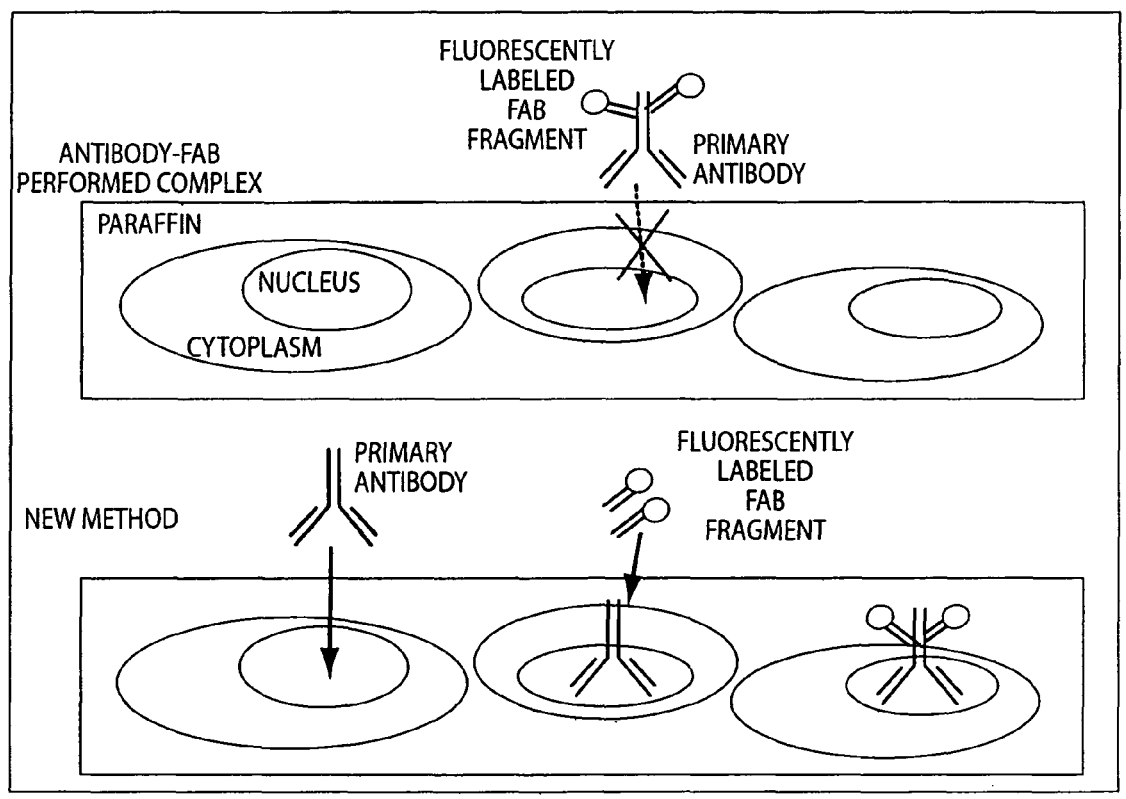
FIG. 1 is a schematic representation of the methods of the invention.
Figure 2:
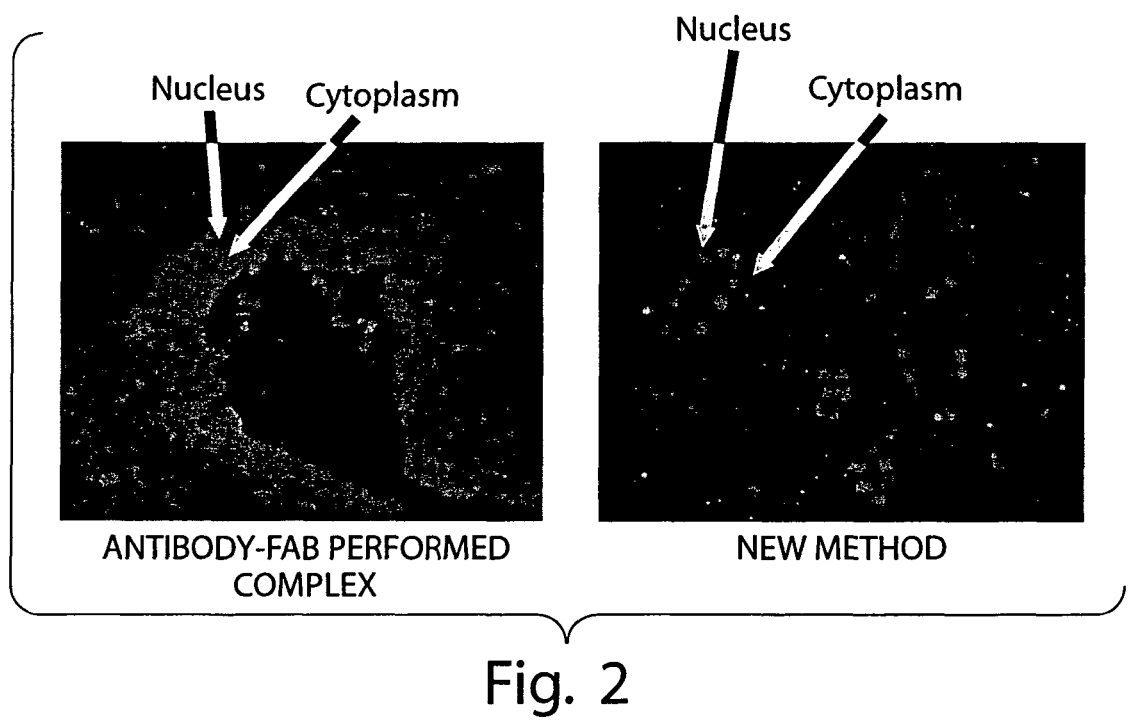
FIG. 2 are photographs showing detection of the androgen receptor in prostate tissue with polyclonal rabbit IgG using conventional methods (left panel) and the methods of the invention (right panel).
Figure 3:
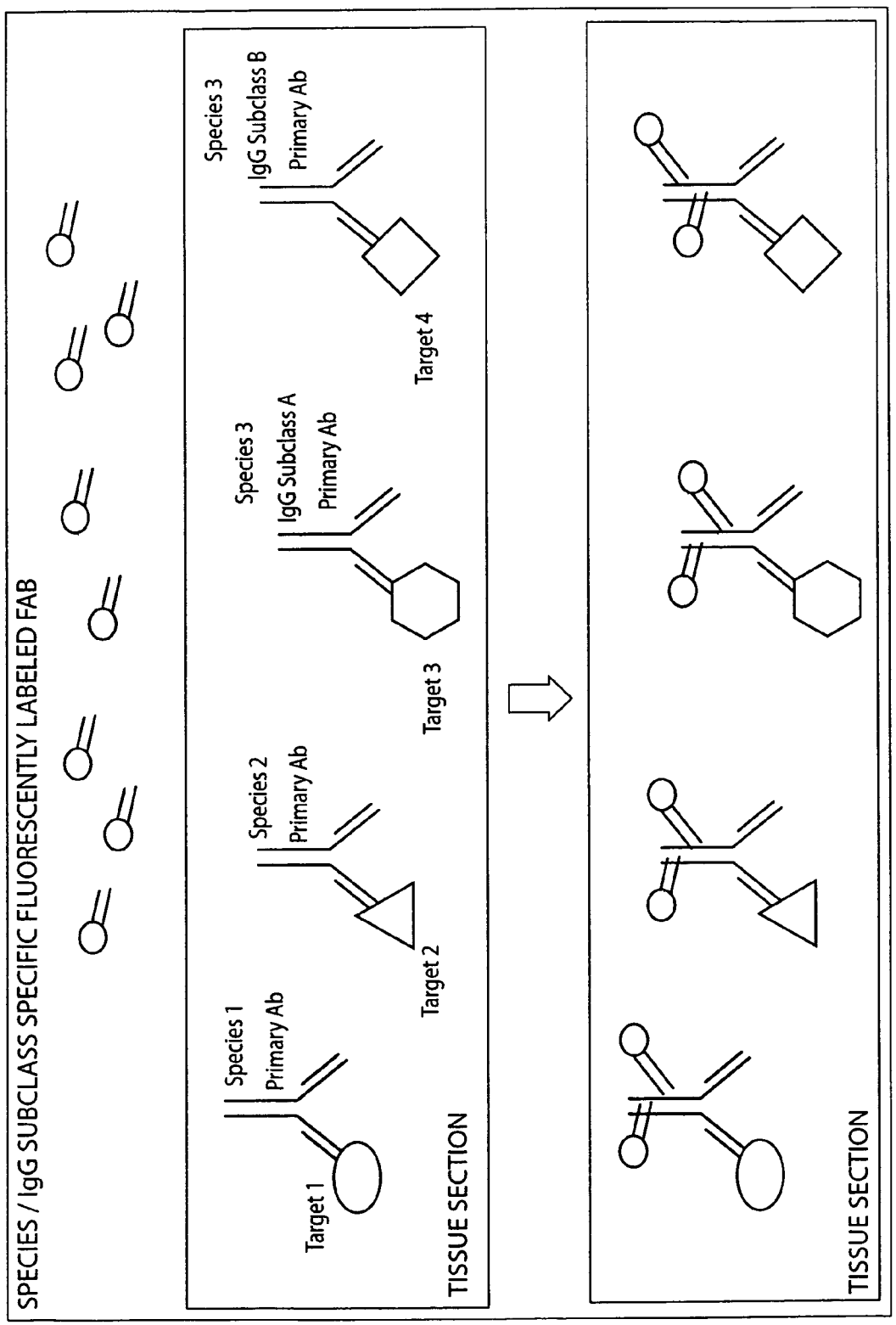
FIG. 3 is a schematic representation of multiplex detection of biomarkers.
Figure 4:
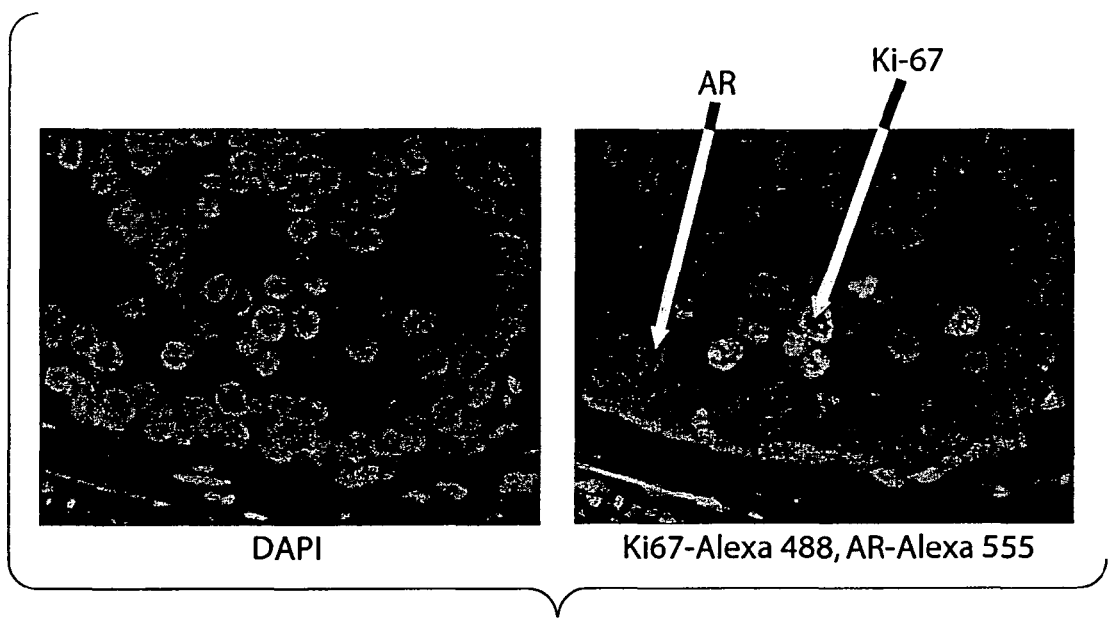
FIG. 4 are photographs showing simultaneous detection of Ki-67 and androgen receptor (AR) with rabbit polyclonal anti AR IgG and mouse monoclonal anti AR IgM.

The invention provides an improved method for the detection of one or more targets in a biological sample. More specifically, the present invention is based on a method of simultaneous in situ analysis of multiple intracellular targets. The methods of the invention allow high spatial resolution for accurate cellular localization of antigen and high spectral resolution to allow simultaneous detection of multiple immunohistochemical stains. The methods are particularly suited for detection of nuclear antigens. The methods are useful in a number of fields, such as, for example, in cancer diagnosis and prognosis.

The present invention is advantageous over previously described methods in that it provides the benefits of indirect labeling with the ease and flexibility of direct labeling for determination of a desired target in a biological sample. Labeling reagents specific for a target-binding antibody are complexed after addition with a biological sample. Labeling reagents according to the present invention typically comprise a monovalent antibody fragment (Fab) that binds to the Fc and/or F(ab')$_2$ portion of primary antibody and is covalently or non-covalently attached to a fluorescent label. Thus, unlike previous described methods, the independently applied labeling reagent does not comprise a bivalent antibody that recognizes the primary antibody, but a much smaller monovalent antibody fragment (Fab) or F(ab')$_2$ that has a greater potential to penetrate formalin fixed, paraffin embedded tissue. Thus, the present invention provides numerous advantages over the conventional methods of immunolabeling.

Definitions

"Affinity" is defined as the strength of the binding interaction of two molecules, such as an antigen and its antibody, which is defined for antibodies and other molecules with more than one binding site as the strength of binding of the ligand at one specified binding site. Although the noncovalent attachment of a ligand to antibody is typically not as strong as a covalent attachment, "High affinity" is for a ligand that binds to an antibody having an affinity constant ($K_a$) of greater than $10^4$ M$^{-1}$, typically $10^5$-$10^{11}$ M$^{-1}$; as determined by inhibition ELISA or an equivalent affinity determined by comparable techniques such as, for example, Scatchard plots or using Kd/dissociation constant, which is the reciprocal of the $K_a$, etc.

"Antibody" is defined as a protein of the immunoglobulin (Ig) superfamily that binds noncovalently to certain substances (e.g. antigens and immunogens) to form an antibody-antigen complex, including but not limited to antibodies produced by hybridoma cell lines, by immunization to elicit a polyclonal antibody response, by chemical synthesis, and by recombinant host cells that have been transformed with an expression vector that encodes the antibody. In humans, the immunoglobulin antibodies are classified as IgA, IgD, IgE, IgG, and IgM and members of each class are said to have the same isotype. Human IgA and IgG isotypes are further subdivided into subtypes IgA$_1$, and IgA$_2$, and IgG$_1$, IgG$_2$, IgG$_3$, and IgG$_4$. Mice have generally the same isotypes as humans, but the IgG isotype is subdivided into IgG$_1$, IgG$_{2a}$, IgG$_{2b}$, and IgG$_3$ subtypes. Thus, it will be understood that the term "antibody" as used herein includes within its scope (a) any of the various classes or sub-classes of immunoglobulin, e.g., IgG, IgM, IgE derived from any of the animals conventionally used and (b) polyclonal and monoclonal antibodies, such as murine, chimeric, or humanized antibodies. Antibody molecules have regions of amino acid sequences that can act as an antigenic determinant, e.g. the Fc region, the kappa light chain, the lambda light chain, the hinge region, etc. An antibody that is generated against a selected region is designated anti-(region), e.g. anti-Fc, anti-kappa light chain, anti-lambda light chain, etc. An antibody is typically generated against an antigen by immunizing an organism with a macromolecule to initiate lymphocyte activation to express the immunoglobulin protein. The term antibody, as used herein, also covers any polypeptide, antibody fragment, or protein having a binding domain that is, or is homologous to, an antibody binding domain, including, without limitation, single-chain Fv molecules (scFv), wherein a VH domain and a VL domain are linked by a peptide linker that allows the two domains to associate to form an antigen binding site (Bird et al., Science 242, 423 (1988) and Huston et al., Proc. Natl. Acad. Sci. USA 85, 5879 (1988)). These can be derived from natural sources, or they may be partly or wholly synthetically produced.

"Antibody fragments" is defined as fragments of antibodies that retain the principal selective binding characteristics of the whole antibody. Particular fragments are well-known in the art, for example, Fab, Fab', and F(ab')$_2$, which are obtained by digestion with various proteases and which lack the Fc fragment of an intact antibody or the so-called "half-molecule" fragments obtained by reductive cleavage of the disulfide bonds connecting the heavy chain components in the intact antibody. Such fragments also include isolated fragments consisting of the light-chain-variable region, "Fv" fragments consisting of the variable regions of the heavy and light chains, and recombinant single chain polypeptide molecules in which light and heavy variable regions are connected by a peptide linker. Other examples of binding fragments include (i) the Fd fragment, consisting of the VH and CH1 domains; (ii) the dAb fragment (Ward, et al., Nature 341, 544 (1989)), which consists of a VH domain; (iii) isolated CDR regions; and (iv) single-chain Fv molecules (scFv) described above. In addition, arbitrary fragments can be made using recombinant technology that retains antigen-recognition characteristics.

"Antigen" is defined as a molecule that induces, or is capable of inducing, the formation of an antibody or to which an antibody binds selectively, including but not limited to a biological material. Antigen also refers to "immunogen". An antibody binds selectively to an antigen when there is a relative lack of cross-reactivity with or interference by other substances present.

"Biological sample" or "Biological material" is defined as a sample retrieved from an animal, mammals and human beings in particular. The sample may be of a healthy tissue, disease tissue or tissue suspected of being disease tissue. The sample may be a biopsy taken, for example, during a surgical procedure. The sample may be collected via means of fine needle aspiration, scraping or washing a cavity to collects cells or tissue therefrom. The sample may be of a tumor e.g., solid and hematopoietic tumors as well as of neighboring healthy tissue. The sample may be a smear of individual cells or a tissue section. Typically, the sample comprises tissue, cell or cells, cell extracts, cell homogenates, purified or reconstituted proteins, recombinant proteins, bodily and other biological fluids, viruses or viral particles, prions, subcellular components, or synthesized proteins. Possible sources of cellular material used to prepare the sample of the invention include without limitation plants, animals, fungi, protists, bacteria, archae, or cell lines derived from such organisms.

"Complex" is defined as two or more molecules held together by noncovalent bonding, which are typically noncovalent combinations of biomolecules such as a protein complexed with another protein. In contrast, a protein is covalently labeled with a substance when there is a covalent chemical bond between the substance and the protein.

"Detectably distinct" is defined as the signal being distinguishable or separable by a physical property either by observation or instrumentally. For example, but not limitation, a fluorophore is readily distinguishable, either by spectral characteristics or by fluorescence intensity, lifetime, polarization or photo-bleaching rate from another fluorophore in the sample, as well as from additional materials that are optionally present.

"Directly detectable" is defined to mean that the presence of a material or the signal generated from the material is immediately detectable by observation, instrumentation, or film without requiring chemical modifications.

"Immunoconjugates" is defined to mean that labeling proteins of the invention, where instead of a detectable label being attached to the protein, a therapeutic agent or drug is attached. The term immunoconjugate is used interchangeably with drug-labeled protein.

"Monovalent antibody fragment" is defined as an antibody fragment that has only one antigen-binding site. Examples of monovalent antibody fragments include, but are not limited to, Fab fragments (no hinge region), Fab' fragments (monovalent fragments that contain a heavy chain hinge region), and single-chain fragment variable (ScFv) proteins.

"Multiplex identification" refers to the simultaneous identification of one or more targets in a single mixture. For example, a two-plex amplification refers to the simultaneous identification, in a single reaction mixture, of two different targets.

"Selectively binds" is defined as the situation in which one member of a specific intra or inter species binding pair will not show any significant binding to molecules other than its specific intra- or inter-species binding partner (e.g., an affinity of about 100-fold less), i.e. minimal cross-reactivity.

Detection Methods

In various aspects the invention provides methods of detecting a target in a biological sample. Targets are detected by contacting a biological sample with a target detection reagent, e.g., an antibody or fragment thereof and a labeling reagent. Targets are detected by the presence or absence of the detection reagent-labeling reagent complex. Preferably, the biological sample is contacted with the target detection reagent and the labeling reagent sequentially. For example, the biological sample is incubated with the detection reagent under conditions that allow a complex between the detection reagent and target to form. After complex formation the biological sample is optionally washed one or more times to remove unbound detection reagent. The biological sample is further contacted with a labeling reagent that specifically binds the detection reagent that is bound to the target. The biological sample is optionally washed one or more times to remove unbound labeling reagent. The presence or absence of the target in the biological sample is then determined by detecting the labeling reagent. Alternatively, the biological sample is contacted with the target detection reagent and the labeling reagent concurrently.

The invention also provides for the detection of multiple targets in a sample. Multiple targets include the discrete epitope that the target-binding antibody has affinity for as well as molecules or structures that the epitiope is bound to. Thus, multiple target identification includes phenotyping of cells based on the concentration of the same cell surface marker on different cells. In this way multiple target identification is not limited to the discrete epitope that the target binding antibody binds, although this is clearly a way that multiple targets can be identified, i.e. based on the affinity of the target-binding antibody.

Multiple targets are identified by contacting the biological sample with additional detection reagents followed by additional labeling reagent specific for the additional detection reagents using the method described above. For example, subsets of labeling reagent are prepared with distinct labels, e.g., fluorophores that are distinguished by their emission spectra, e.g., one that emits in the green spectra and one that emits in the red spectra. The labeling reagent subsets are then added to the biological sample containing detection reagent-target complexes in a controlled ratio, e.g., two parts one labeling reagent (e.g., green emission) and one part the other labeling reagent (e.g., red emission) per target binding antibody. In this way the immuno-labeled complexes can be used to detect a target. If another immuno-labeled complex were added to the sample the original target could be distinguished from the subsequently detected target.

In alternative methods, two or more targets are identified in a biological sample by premixing a first detection reagent with a first labeling reagent to form a first complex. Optionally, after complex formation mixture is purified to remove uncomplexed detection reagent and labeling reagent. The biological sample is incubated with the first complex and a second detection reagent. Optionally, 3, 4, 5, 6, 7, 8, 9, 10 or more targets are detected in a sample. Depending upon the number of targets to be detected, 3, 4, 5, 6, 7, 8, 9, 10 or more detection reagents may be used. Subsequently, the biological sample is incubated with a second labeling reagent that specifically binds the second detection reagent that is bound to the second target. Optionally, prior to incubation with the second labeling reagent the biological sample is washed one or more times to remove unbound first complex and second detection reagent. The presence or absence of the target in the biological sample is then determined by detecting the labeling reagent. Optionally, prior to detecting the labeling reagent the biological sample is washed one or more times to remove unbound labeling reagents.

The sample is defined to include any material that may contain a target to which an antibody has affinity. Typically the sample is biological in origin and comprises tissue, cell or a population of cells, cell extracts, cell homogenates, purified or reconstituted proteins, recombinant proteins, bodily and other biological fluids, viruses or viral particles, prions, subcellular components, or synthesized proteins. The sample is a biological fluid such as whole blood, plasma, serum, nasal secretions, sputum, saliva, urine, sweat, transdermal exudates, or cerebrospinal fluid. Alternatively, the sample may be whole organs, tissue or cells from an animal. Examples of sources of such samples include muscle, eye, skin, gonads, lymph nodes, heart, brain, lung, liver, kidney, spleen, solid tumors, macrophages, or mesothelium. The sample is prepared in a way that makes the target, which is determined by the end user, in the sample accessible to the immuno-labeled complexes. Typically, the samples used in the invention are comprised of tissue or cells. Preferably, the tissue or cells to be assayed will be obtained by surgical procedures, e.g., biopsy. The tissue or cells are fixed, or frozen to permit histological sectioning. In situ detection is used to determine the presence of a particular target and to determine the distribution of the target in the examined tissue. General techniques of in situ detection are well known to those of ordinary skill. See, for example, Ponder, "Cell Marking Techniques and Their Application," in Mammalian Development: A Practical Approach, Monk (ed.), 115 (1987). Treatments that permeabilize the plasma membrane, such as electroporation, shock treatments, or high extracellular ATP, can be used to introduce reagents into cells.

The methods of the invention provides significant advantages over existing technology in that they do not rely on nucleic acid hybridizations. Therefore, the methods of the invention can be performed in the presence of nucleases e.g., non-specific nucleases, DNase and RNase.

The target is any compound of biological or synthetic origin that is present as a molecule or as a group of molecules. Typically, the target is a biological material or antigenic determinant. The chemical identity of the target antigen may be known or unknown. Biological materials include, but are not limited to, antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatized nucleic acids (including deoxyribo- and ribonucleic acids and peptide nucleic acids), DNA and RNA fragments and derivatized fragments (including single and multi-stranded fragments), natural and synthetic drugs, receptors, virus particles, bacterial particles, virus components, biological cells, cellular components (including cellular membranes and organelles), natural and synthetic lipid vesicles, and polymer membranes. Typically the target material is present as a component or contaminant of a sample taken from a biological or environmental system.

The target is transmembrane marker. Alternatively, the target is an intracellular or a nuclear antigen. Intracellular antigen include, for example, alpha-fetoprotein (AFP), human chorionic gonadotropin (HCG), colon-specific antigen-p (CSAp), prostatic acid phosphatase, pancreatic oncofetal antigen, placental alkaline phosphatase, parathormone, calcitonin, tissue polypeptide antigen, galactosyl transferase-II (GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA), pMTOR, pAKT, PSMA, prostate specific antigen (PSA), x-methylacyl-CoA racemase (AMACR), vascular endothelial growth factor (VEGF), and tumor angiogenesis factor (TAF). Nuclear antigens include for example, PTEN, Ki67, Cyclin D1, EZH2, p53, IGFBP2, p-STAT-3. Other targets include those listed on Tables 1 and 2 below.

The detection reagent is a compound that is capable of specifically binding to the target of interest. The detection reagent is selected based on the desired target. The detection reagent is for example a polypeptide such as a target specific antibody or fragment thereof. As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, polyclonal, monoclonal, chimeric, single chain, $F_{ab}$, $F_{ab'}$ and $F_{(ab')2}$ fragments, and an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

Monoclonal antibodies are particularly advantageous in practicing the methods of the present invention. Generally, monoclonal antibodies are more sensitive and specific than polyclonal antibodies. In addition, unlike polyclonal antibodies, which depend upon the longevity of the animal producing the antibody, the supply of monoclonal antibodies is indefinite. Polyclonal antibodies however, are useful when it is necessary to use antibodies with multiple isotypes, as generally most monoclonal antibodies are of the IgG1 subclass.

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three-dimensional structural characteristics, as well as specific charge characteristics.

As used herein, the terms "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

The labeling reagent contains an antibody binding moiety and a detection moiety. The antibody binding moiety and the detection moiety are covalently linked. Alternatively, the antibody binding moiety and the detection moiety are non-covalently linked.

The antibody binding moiety bind selectively and with high affinity to a selected region of the detection reagent, e.g., the target-binding antibody. The binding region for the antibody binding moiety may be a selected peptide linker (including the J region), light chain or heavy chain of the target-binding antibody; preferably the labeling protein binds the Fc region of the target-binding antibody.

The antibody binding moiety is an antibody or fragment thereof, such as, but not limited to, anti-Fc, an anti-Fc isotype, anti-J chain, anti-kappa light chain, anti-lambda light chain, or a single-chain fragment variable protein. Preferably, the antibody binding moiety is monovalent. Alternatively, the antibody binding moiety is a non-antibody peptide or protein, such as, for example but not limited to, soluble Fc receptor, protein G, protein A, protein L, lectins, or a fragment thereof. Optionally, the non-antibody protein or peptide is coupled with albumin such as human and bovine serum albumins or ovalbumin.

Typically, the antibody binding moiety is a Fab fragment specific to the Fc portion of the target-binding antibody or to an isotype of the Fc portion of the target-binding antibody. The monovalent Fab fragments are produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$.

The detection moiety, i.e., label, is any substance used to facilitate identification and/or quantitation of a target. Detection moieties are directly observed or measured or indirectly observed or measured. Detection moieties include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The detection moiety can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The detection moiety may also take the form of a chemical or biochemical, or an inert particle, including but not limited to colloidal gold, microspheres, quantum dots, or inorganic crystals such as nanocrystals or phosphors (see, e.g., Beverloo, et al., Anal. Biochem. 203, 326-34 (1992)). The term detection moiety can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP. Similarly, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other labels that are described in the Molecular Probes Handbook Of Fluorescent Probes And Research Chemicals by Richard P. Haugland, 6th Ed., (1996), and its subsequent 7th edition and 8th edition updates issued on CD Rom in November 1999 and May 2001, respectively, the contents of which are incorporated by reference, and in other published sources.

A fluorophore is any chemical moiety that exhibits an absorption maximum beyond 280 nm, and when covalently attached to a labeling reagent retains its spectral properties. Fluorophores include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569,587; 5,569,766; 5,486,616; 5,627,027; 5,808,044; 5,877,310; 6,002,003; 6,004,536; 6,008,373; 6,043,025; 6,127,134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. No. 6,162,931; 6,130,101; 6,229,055; 6,339,392; 5,451,343 and U.S. Ser. No. 09/922,333), an oxazine (including any corresponding compounds disclosed in U.S. Pat. No. 4,714,763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459,276; 5,501,980 and 5,830,912), a benzofuran (including an corresponding compounds disclosed in U.S. Pat. Nos. 4,603,209 and 4,849,362) and benzphenalenone (including any corresponding compounds disclosed in U.S. Pat. No. 4,812,409) and derivatives thereof. As used herein, oxazines include resorufins (including any corresponding compounds disclosed in U.S. Pat. No. 5,242,805), aminooxazinones, diaminooxazines, and their benzo-substituted analogs.

When the fluorophore is a xanthene, the fluorophore is optionally a fluorescein, a rhodol (including any corresponding compounds disclosed in U.S. Pat. Nos. 5,227,487 and 5,442,045), or a rhodamine (including any corresponding compounds in U.S. Pat. Nos. 5,798,276; 5,846,737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945,171). Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position. Preferred fluorophores of the invention include xanthene (rhodol, rhodamine, fluorescein and derivatives thereof) coumarin, cyanine, pyrene, oxazine and borapolyazaindacene. Most preferred are sulfonated xanthenes, fluorinated xanthenes, sulfonated coumarins, fluorinated coumarins and sulfonated cyanines. The choice of the fluorophore attached to the labeling reagent will determine the absorption and fluorescence emission properties of the labeling reagent and immuno-labeled complex. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

In one aspect of the invention, the fluorophore has an absorption maximum beyond 480 nm. In a particularly useful embodiment, the fluorophore absorbs at or near 488 nm to 514 nm (particularly suitable for excitation by the output of the argon-ion laser excitation source) or near 546 nm (particularly suitable for excitation by a mercury arc lamp).

Preferably the detection moiety is a fluorescent dye. The fluorescent dye include for example Fluorescein, Rhodamine, Texas Red, Cy2, Cy3, Cy5, Cy0, Cy0.5, Cy1, Cy1.5, Cy3.5, Cy7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-(6-(7-nitrobenz-2-oxa-1,3-diazol-4-yl)amino)caproyl) (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

Many of fluorophores can also function as chromophores and thus the described fluorophores are also preferred chromophores.

In addition to fluorophores, enzymes also find use as detectable moieties. Enzymes are desirable detectable moieties because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art, many of which are described in the MOLECULAR PROBES HANDBOOK, supra.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazol-e (AEC), which yield a distinguishing color (brown and red, respectively). Other colorimetric oxidoreductase substrates that yield detectable products include, but are not limited to: 2,2-azino-bis(3-ethylbenzothiaz-oline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplexe Red reagent and its variants (U.S. Pat. No. 4,384, 042) and reduced dihydroxanthenes, including dihydrofluoresceins (U.S. Pat. No. 6,162,931) and dihydrorhodamines including dihydrorhodamine 123. Peroxidase substrates that are tyramides (U.S. Pat. Nos. 5,196,306; 5,583,001 and 5,731,158) represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples that are cells, tissues or arrays for their subsequent detection by microscopy, flow cytometry, optical scanning and fluorometry.

Additional colorimetric (and in some cases fluorogenic) substrate and enzyme combination use a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy4-methylcoumarinyl phosphate (DiFMUP, U.S. Pat. No. 5,830,912) fluorescein diphosphate, 3-0-methylfluorescein phosphate, resorufin phosphate, 9H-(1,3-dichloro-9, 9-dimethylacridin-2-one-7-yl) phosphate (DDAO phosphate), or ELF 97, ELF 39 or related phosphates (U.S. Pat. Nos. 5,316,906 and 5,443,986).

Glycosidases, in particular beta-galactosidase, beta-glucuronidase and beta-glucosidase, are additional suitable enzymes. Appropriate colorimetric substrates include, but are not limited to, 5-bromo4-chloro-3-indolyl beta-D-galactopyranoside (X-gal) and similar indolyl galactosides, glucosides, and glucuronides, o-nitrophenyl beta-D-galactopyranoside (ONPG) and p-nitrophenyl beta-D-galactopyranosid-e. Preferred fluorogenic substrates include resorufin beta-D-galactopyranoside, fluorescein digalactoside (FDG), fluorescein diglucuronide and their structural variants (U.S. Pat. Nos. 5,208,148; 5,242,805; 5,362,628; 5,576,424 and 5,773,236), 4-methylumbelliferyl beta-D-galactopyranoside, carboxyumbelliferyl beta-D-galactopyranoside and fluorinated coumarin beta-D-galactopyranosides (U.S. Pat. No. 5,830,912).

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. For example, the enzyme is luciferase or aequorin. The substrates are luciferine, ATP, $Ca^{++}$ and coelenterazine.

In addition to enzymes, haptens such as biotin are useful detectable moieties. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, or nucleotides.

A detectable moiety is a fluorescent protein. Exemplary fluorescent proteins include green fluorescent protein (GFP) the phycobiliproteins and the derivatives thereof, luciferase or aequorin. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra. This is particularly advantageous for detecting a low quantity of a target in a sample wherein the emitted fluorescent light is maximally optimized, in other words little to none of the emitted light is reabsorbed by the fluorescent protein. For this to work, the fluorescent protein and fluorophore function as an energy transfer pair wherein the fluorescent protein emits at the wavelength that the fluorophore absorbs at and the fluorphore then emits at a wavelength farther from the fluorescent proteins than could have been obtained with only the fluorescent protein. A particularly useful combination is the phycobiliproteins disclosed in U.S. Pat. Nos. 4,520,110; 4,859,582; 5,055,556 and the sulforhodamine fluorophores disclosed in U.S. Pat. No. 5,798, 276, or the sulfonated cyanine fluorophores disclosed in U.S. Ser. Nos. 09/968/401 and 09/969/853; or the sulfonated xanthene derivatives disclosed in U.S. Pat. No. 6,130,101 and those combinations disclosed in U.S. Pat. No. 4,542,104. Alternatively, the fluorophore functions as the energy donor and the fluorescent protein is the energy acceptor.

Preparation of labeling reagent using low molecular weight reactive dyes is known by those of skill in the art and is well documented, e.g., by Richard P. Haugland, Molecular Probes Handbook Of Fluorescent Probes And Research Chemicals, Chapters 1-3 (1996) and by Brinkley, Bioconjugate Chem. 3, 2 (1992). Labeling proteins typically result from mixing appropriate reactive dyes and the protein to be conjugated in a suitable solvent in which both are soluble. The majority of the preferred dyes of the invention are readily soluble in aqueous solutions, facilitating conjugation reactions with most biological materials. For those reactive dyes that are photoactivated, conjugation requires illumination of the reaction mixture to activate the reactive dye.

Methods of visualizing the detection moiety depend on the label.

At any time after addition of the immuno-labeled complex to the sample, the sample is illuminated with a wavelength of light selected to give a detectable optical response, and observed with a means for detecting the optical response. Equipment that is useful for illuminating the fluorescent compounds of the present invention includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard or expected response, indicates whether and to what degree the sample possesses a given characteristic, i.e. desired target.

The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

When an indirectly detectable label is used then the step of illuminating typically includes the addition of a reagent that facilitates a detectable signal such as colorimetric enzyme substrate. Radioisotopes are also considered indirectly detectable wherein an additional reagent is not required but instead the radioisotope must be exposed to X-ray film or some other mechanism for recording and measuring the radioisotope signal. This can also be true for some chemiluminescent signals that are best observed after expose to film.

Application

One embodiment of the invention is directed to a method of detecting a target epitope in a biological sample. The method may be, for example, an immunohistochemical detection method. The epitope may be any epitope in an antigen. The antigen may be any tissue antigen including, for example, a nuclear antigen, a cytoplasmic antigen, or a membrane bound antigen. The method comprises the following steps. First, a biological sample is contacted with a first antibody specific for an epitope in the biological sample. The contacting may involve, for example, incubating the sample in PBS and adding a first antibody, suspended in PBS, to the sample. Because the first antibody is specific for the target epitope, it will be bound only at the location where the epitope is present. The biological sample may be any sample useful for immunohistochemical detection including tissue samples, tissue sections, and cultured cells of both eukaryotic and prokaryotic origin. The tissue section may be formalin fixed sections or frozen sections. The tissue sections may be embedded, for example, in a solidifying agent such as paraffin or plastic. After an appropriate incubation period which may include an incubation with agitation (e.g., shaking or rocking), unbound first antibodies may be removed from the tissue section by washing the section with PBS or another appropriate buffer (a first washing step). Washing may be performed, for example, by incubating (with shaking or rocking) the tissue section in containers with PBS.

Following the removal of unbound first antibodies, the first antibody bound biological sample is contacted with a Fab fragment (labeling protein) of second antibodies directed against their Fc regions of the first antibody. The Fab fragment is labeled with a detectable label. In a preferred embodiment, the Fab fragment is a Zenon™ reagent (Invitrogen, Carlsbad, Calif.). For example, if the first antibody is a mouse IgG, the second antibody may be a goat-anti-mouse IgG antibody. The Fab fragment will bind to the first antibody to produce a Fab bound first antibody.

The label on the Fab fragment may be directly detected without a washing step. The distribution of the label will correspond to the distribution of the epitope. If the detectable label is a fluorescent moiety, the label may be detected using a fluorescence microscope. The use of a fluorescence microscope for the detection of labeled tissue section is well known.

Optionally, the tissue section may be washed to remove unbound Fab fragments before the label is detected. The washing step may comprise the same steps as the first washing step described above.

The target epitope may be any epitope in a cell, including, for example an epitope on an antigen. The antigen may be an oncoprotein (e.g. bcl-2, c-erbB-2) or a protein that is indicative of tumor cell heterogeneity (p53). Useful antigens include, for example, epitopes for the androgen receptor (AR), Cytokeration 18 or PTEN.

In a preferred embodiment, the first antibody penetrates the tissue section and is bound to an epitope in the interior of the section. The addition of the Fab fragment allows the formation of a first antibody-Fab complex within the tissue section.

Multiplex Application

The methods of the invention may be used to detect a plurality (at least two) of targets (epitopes) in a biological sample using the following steps:

Step A A first antibody specific for a first target is saturated with labeling protein to create a pre-formed complex.

Step B Excess labeling protein is removed after the formation of the pre-formed complex (e.g., by gel filtration).

Step C The pre-formed complex is contacted to a biological sample.

Step D A second antibody specific for a second target is contacted to the same biological sample. The second antibody is not labeled and is not complexed with a labeling protein. Step D may be performed before, after or simultaneously with Step C.

Step E Excess antibody and excess pre-formed complex may be removed in an optional wash step.

Step F A second labeling protein which is at least specific to the second antibody, is applied to the biological sample.

Figure 5:
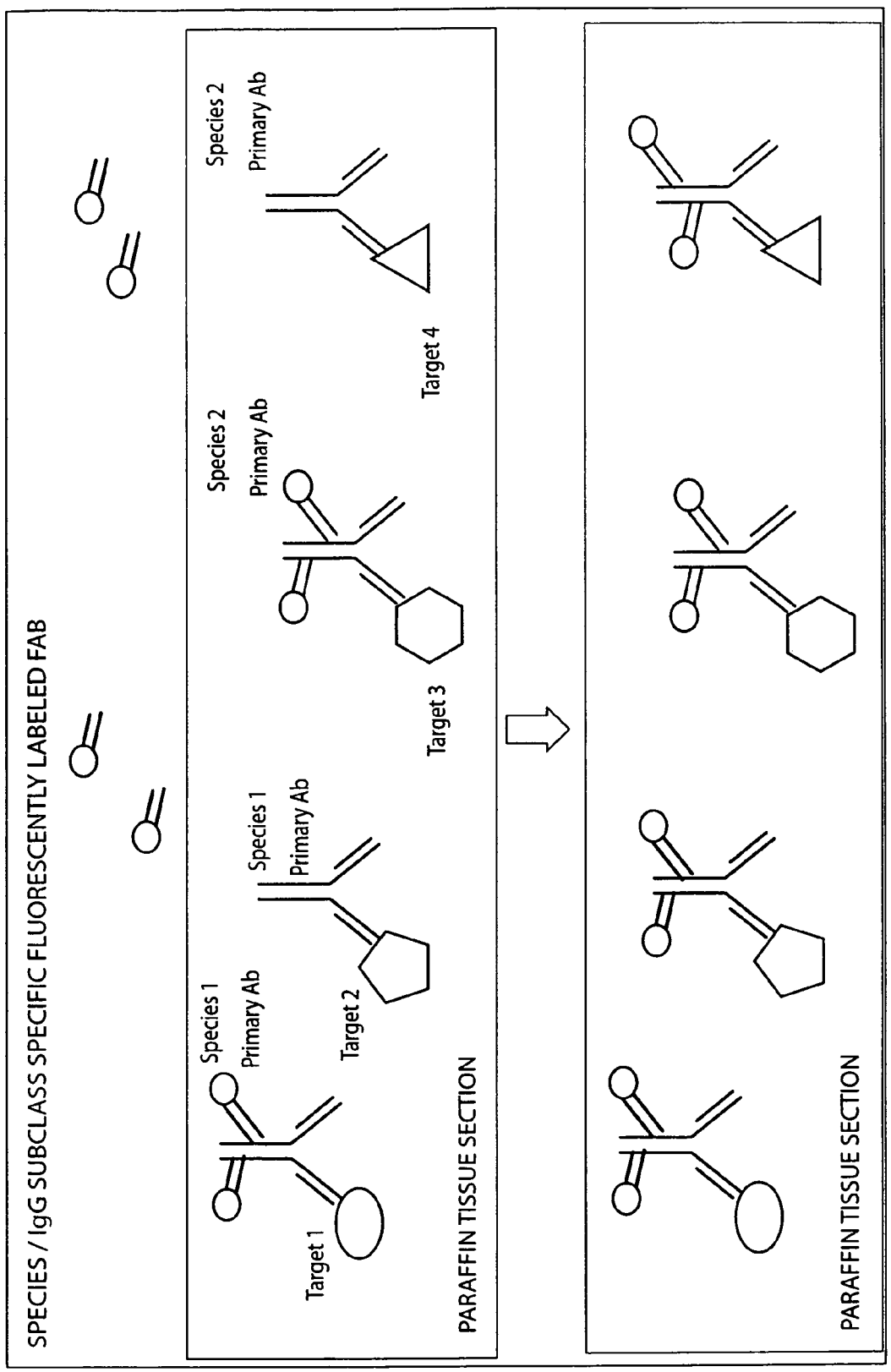
FIG. 5 is a schematic representation of multiplex detection of biomarkers in paraffin-embedded tissue sections.
Figure 6:
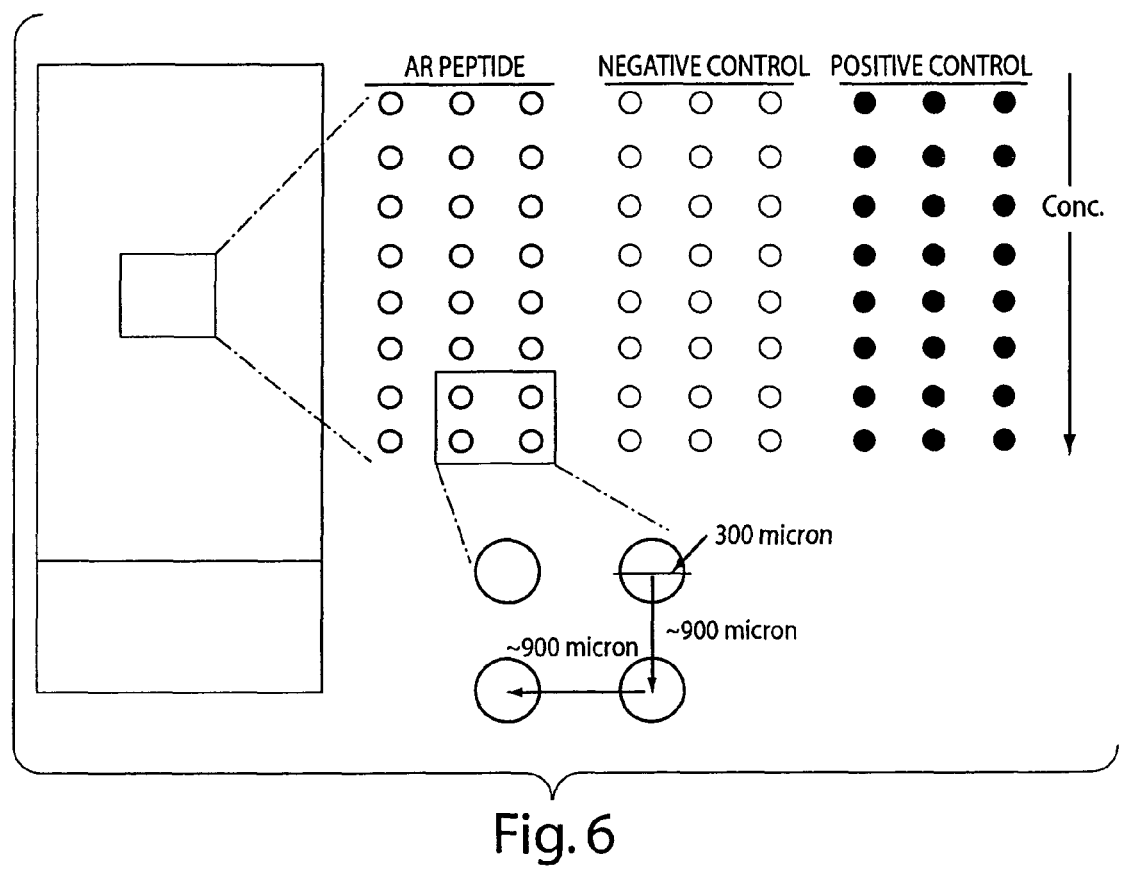
FIG. 6 is a schematic representation of the use of a peptide array to quantify biomarker expression.
Figure 7:
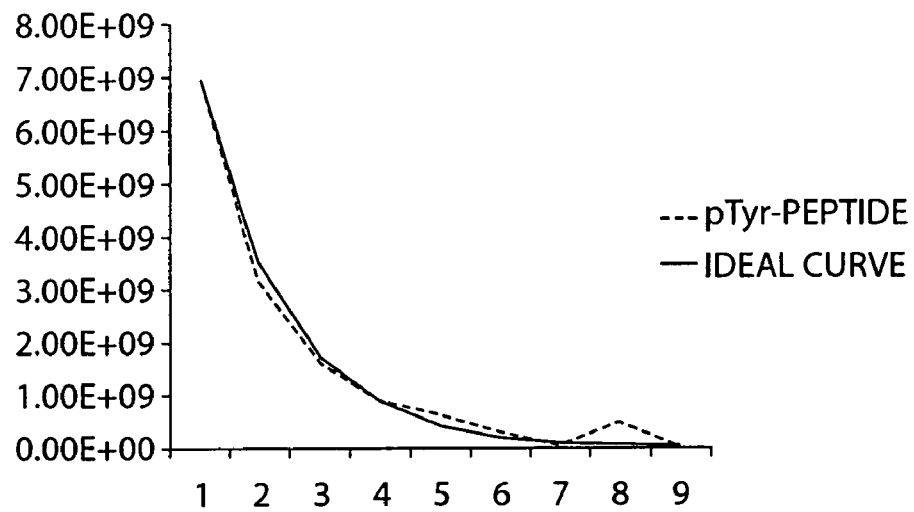
FIG. 7 is a graph showing pTyr peptide array standard curve.
Figure 8:
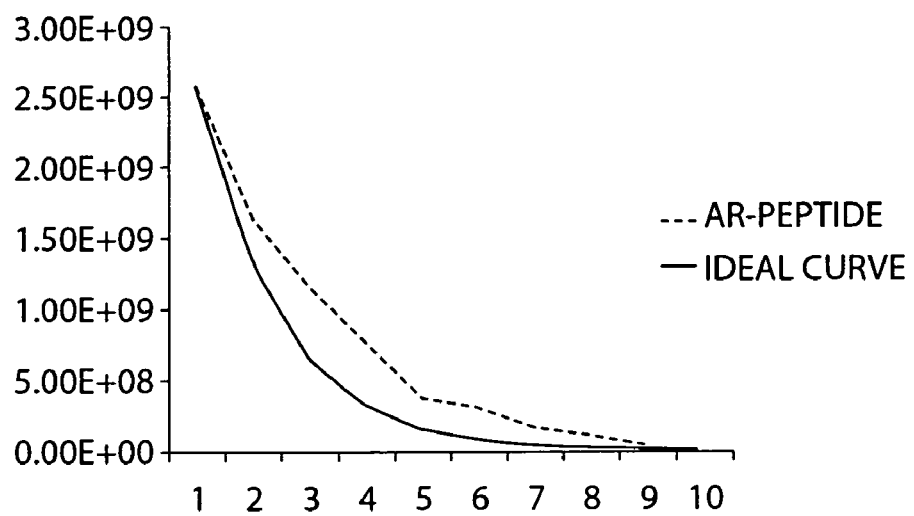
FIG. 8 is a graph showing AR peptide array standard curve.
Figure 9:
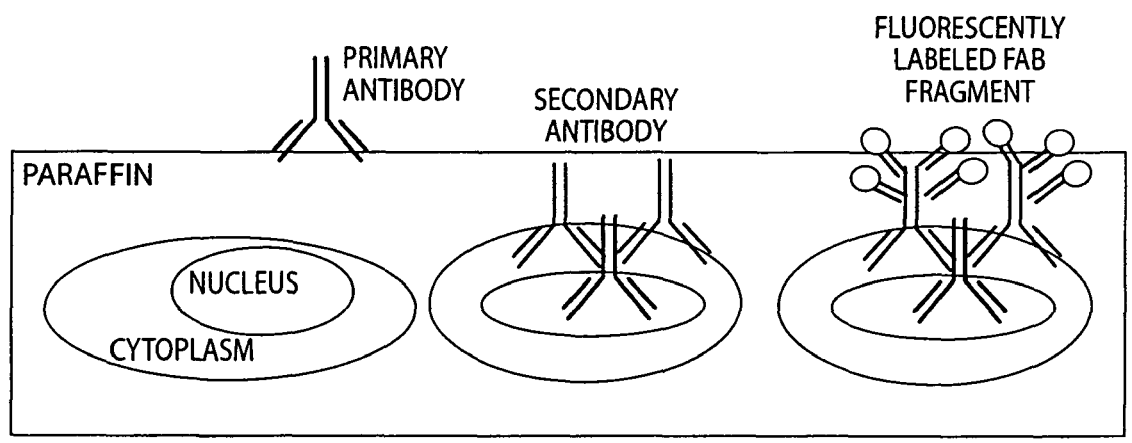
FIG. 9 is a schematic representation of amplified the methods of the invention.

In the above method, the second labeling protein that is added in Step F will only bind to the second antibody, because all potential binding sites on the first antibody will already be saturated with fluorescently labeled Fab fragment (see FIG. 5).

Since the first antibody is applied as a pre-formed complex, it is preferred that the first antibody is specific for a nuclear antigen where tissue penetration has been found to be less critical for the detection.

This "multiplexed" detection (described in Example 1) can be further multiplexed by two alternative methods. In alternative method 1, Step A may involve the production of a "first antibody/first labeling protein complex" and a "third antibody/third labeling complex" made in separate reaction vessels. Both the first complex and third complex may be applied in Step C. The result would be a biological sample labeled with three different antibody/labeling proteins complexes (i.e., $1^{st}$ antibody/$1^{st}$ labeling protein; $2^{nd}$ antibody/$2^{nd}$ labeling protein; $3^{rd}$ antibody/$3^{rd}$ labeling protein). If the first, second and third labeling protein comprises detectably different labels, then a total of three different labels may be detected on the biological sample.

In alternative method 2, a second antibody and a third antibody may be added in Step D wherein the second antibody and the third antibody is specific for different targets. In step F, a second and a third labeling protein may be added. The second labeling protein is specific for the second antibody while the third labeling protein is specific for the third antibody. For example, the second antibody and the third antibody may be from different IgG subclasses and the second and third labeling proteins may be IgG subclass specific. Using this method, a total of three different labels may be detected on the biological sample.

While alternative method 1 and alternative method 2 described above describe the use of two pre-formed complexes (Step B) or two antibodies (Step D), it is understood that the method of the invention is not limited to two pre-formed complexes or two antibodies. Any number of pre-formed complexes or antibodies may be used in the method of the invention. Further, alternative method 1 and alternative method 2 may be combined. For example, if alternative method 1 and alternative method 2 as describe above were combined, a total of four different targets in a biological sample may be detected. Additionally if alternative method 1 and alternative method 2 are combined, alternative method 2 may be repeated as to detect a total of seven or more different targets in a biological sample.

For all the methods of the invention, unbound immunolabeling complexes that do not bind to the target may be optionally removed from the sample by conventional methods, such as washing. In an optional step for all the methods of the invention, the bound immunolabeling complexes that bind to the target can be fixed in place with the usual fixatives (e.g. formaldehyde, glutaraldehyde) and fixation methods. Fixation can be utilized to improve the durability of the sample and to prevent transfer of the noncovalently complexed labeling protein to other targeting antibodies in the sample that have the same specific binding region.

Another embodiment of the invention is directed to a method for determining a difference in the amount of distribution of an antigen in a tissue section from a tissue to be tested relative to the amount and distribution of said antigen in a tissue section from a normal tissue. Such a comparison can be used to determine if a sample shows an abnormal distribution of epitopes or antigens. First, the method involves the step of detecting a distribution of an epitope in a first sample using any one of the methods of this disclosure. Second, a distribution of an epitope in a normal sample is detected using any one of the methods of this disclosure. Third, the distribution of epitopes or antigens of the first sample and the normal sample is compared to determine if there is a difference in distribution between the two samples.

Another embodiment of the invention is directed to a method for in situ analysis of a biological sample. First, a first antibody which is specific for a first epitope is contacted with a first Fab which is specific for the Fc portion of the first antibody to produce a first antibody-Fab complex. Excess Fab, not bound to the first antibody may be removed in an optional step. The biological sample is then contacted with this first antibody-Fab complex and a second antibody which is specific for a second epitope to generate an antibody biological sample. In an optional step, unbound first antibody-Fab complex and unbound second antibody may be removed by washing. A second Fab, comprising a second detectable label distinguishable from the first detectable label is then contacted to the biological sample. The second Fab is specific for the Fc portion of the second antibody and forms an antibody-Fab complex with the second antibody.

In an optional step, excess second Fab may be removed by washing. In the final step, the first and second detectable labels are detected to determine the location and distribution of the epitopes. It is understood that each detectable label is individually detectable in a presence of all others detectable labels in the biological sample.

In still another embodiment of the invention, a platform for multiplexed quantitative antigen assessment is provided that combines immunofluorescence (IF) detection with computer-assisted image analysis. Computing equipment (hardware and/or software) measures the presence, intensity, and/or distribution of fluorescent label(s) in tissue images that result from IF detection, where each label in an image indicates the presence of a target antigen. This computing equipment may include, for example, the commercially-available Definiens Cellenger Developer Studio (v. 4.0) adapted to segment and classify the tissue images into objects (e.g., stroma, lumen, nuclei, cytoplasm, etc.) and/or to detect the fluorescent labels (FIGS. 10A, 11A, 19, and 20). The Definiens Cellenger product can be further designed and adapted to execute scripts that measure the presence, intensity, and/or distribution of the fluorescent labels localized within specified tissue cellular compartments (e.g., such as, the fluorescent labels within nuclei or epithelial cells). These measurements (alone or in combination with other observations such as clinical, molecular, and/or morphometric observations) can be subject to supervised mathematical approaches, including machine learning methods such as support vector regression for censored data (SVRc), in order to generate models for (for example) diagnosis and prognosis of disease. Methods and systems for generating models and for extracting measurements from tissue images are described in commonly-owned U.S. Publication No. 20050262031, which is incorporated by reference herein in its entirety.

Tissue samples processed with the IF detection methods described herein are placed on a Nikon 90i automated fluorescent microscope. Fluorescent images are acquired using a CRI Nuance multispectral camera (Cambridge Research & Instrumentation, Inc.) mounted on the microscope and controlled by MetaMorph online software. Other suitable equipment for image acquisition can be used without departing from the scope and spirit of the present invention. The following description illustrates the usage of IF image acquisition and analysis in order to detect the presence of Androgen Receptor (AR) in tissue. A focus of the study was to identify factors linked to prostate cancer growth and progression.

DAPI (4'-6-Diamidino-2-phenylindole), coupled with the antibodies for Cytokeratin 18 (CK) (DAPI for nuclei and CK18 for epithelial cells), and the Androgen Receptor were applied to tissue on tissue micro-array (TMA) slides. Fluorescent images representing each of the TMA cores were acquired using the equipment described above. More particularly, 12-bit DAPI images were captured with the camera set at 480 nm using a 50% saturation setting. CK 18, labeled with Alexa 488, was acquired using a FITC bandpass filter (Chroma). 12-bit images in 10 nm increments were captured starting 520 nm. AR, labeled with Alexa 568 was captured using a longpass filter (Chroma). 12-bit images in 10 nm increments were captured starting at 570 nm. Image stacks were unmixed using the CRI analysis software. Pure Alexa 488 and 568 dye were used as reference spectra for the unmixing process. Typical regions of autofluorescence and other fluorescent objects (e.g. erythocytes) were assigned to spectral profiles. After completion of the unmixing process, quantitative gray-scale tiff images were stored for the analysis. After unimixing the gray-scale images are combined in order to produce a composite image for analysis by the Definiens Cellenger scripts. When the images are combined, unique fragment and donor ID's are used that associate the images with a patient.

The Definiens Cellenger scripts segment and classify the images in order to detect and quantify the AR signal present within epithelial cell nuclei. Measurements were also taken based biomarker intensities and nuclear areas defined by DAPI segmentation, where the measurements reflected the overall intensity and distribution of AR present in specific cell types. The table below includes a list of the measurements derived from the images is provided in the table below.

| Immunofluorescent Quantitative Androgen Receptor Features | |
|---|---|
| Features | Definition |
| averageip0001 | Average AR marker Intensity in epithelial nuclei |
| averageip0002 | Average AR Intensity in epithelial and stromal Nuclei |
| averageipstroma0003 | Average AR marker Intensity in stromal nuclei |
| maxip0007 | Max AR intensity in epithelial nuclei |
| maxip0008 objects | Max AR intensity in epithelial and stromal nuclei |
| maxipstroma0009 | Max AR intensity in stromal nuclei |
| minip0010 | Min AR intensity epithelial nuclei |
| minip0011 | Min AR intensity in stomal and eputhelial nuclei |
| minipstroma0012 | Min AR stromal nuclei |
| ratioareaepithnucversusepith0013 | Area of epthelial nuclei with AR positive/Area of epithelial nuclei with AR negative |
| correlaobject10005 | Linear correlation coefficient between DAPI and AR images |

From the list of derived measurements for AR, it was determined by supervised mathematical approaches that the 'ratioareaepithnucversusepith0013' feature was independently associated with PSA recurrence when analyzed univariately. This feature represents the ratio of the areas of epithelial nuclei positively and negatively expressed with AR. Thus, this data suggests (for example) that the total amount of AR present in both tumor and non-tumor elements is an important factor in prostate cancer growth and progression.

REFERENCES

Tuson, J. R.; Pascoe, E. W.; Jacob, D. A. (1990) A novel immunohistochemical technique for demonstration of specific binding of human monoclonal antibodies to human cryostat tissue sections. J Histochem Cytochem 38:923-6.

Brown, J. K.; Pemberton, A. D.; Wright, S. H.; Miller, H. R. (2004) Primary antibody-Fab fragment complexes: a flexible alternative to traditional direct and indirect immunolabeling techniques. J Histochem Cytochem. 52:1219-30.

EXAMPLES

Example 1

General Sample Preparation Methods

The following methods are generally used to during the Multiplex detection methods according to the invention Antizen Retrieval:
1. De-paraffinize and re-hydrate the tissue samples as per the standard Leica 5020 SOP.
2. Pre-heat 250 ml of 1× Reveal antigen retrieval solution to boiling in water bath in microwave (heat solution for seven (7) minutes at power level seven (7)).
3. Place slides in container of boiling 1× Reveal solution. Allow to boil for 8.0 minutes as described above.
4. When completed, remove container from microwave water bath and allow to cool for 20 minutes.
5. Rinse slides in PBS briefly followed by 1×5 minutes at room temperature.
6. Place slides on Nemesis 7200 and begin auto-staining program.

Tissue Permeabilization:
Incubate slides in PBT (PBS with 0.2% Triton-X) for 30 minutes. PBT is made as follows:

| Reagent | Vendor | Catalog # | Dilution/ [Conc.] | Amount | Final Volume |
|---|---|---|---|---|---|
| Difco FA Buffer | Fisher | 223142 | 1X | 1.0 g | |
| Triton-X 100 | Fisher | BP151-500 | 0.2% | 2.0 ml | |
| 20% Tween 20 | BioCare | TWN20H | 1.0% | 50.0 ml | |
| ddH2O | — | — | — | 948.0 ml | 1000 ml |

Autofluorescence Removal:
Incubate slides in acid alcohol (1% HCL in 70% EtOH) for 20 minutes. Acid alcohol is made as follows:

| Reagent | Vendor | Catalog # | Dilution/ [Conc.] | Amount | Final Volume |
|---|---|---|---|---|---|
| 200 proof EtOH | Sigma | E7023-4L | 140 proof | 7.28 ml | |
| HCl | Fisher | A144S-500 | 1.0% | 0.1 ml | |
| 20% Tween 20 | BioCare | TWN20H | 1.0% | 0.52 ml | |
| ddH2O | — | — | — | 2.5 ml | 10.4 ml |

Pre-Antibody Treatment Steps

To help permeate the cellular structures of the tissue, the samples were incubated in PBS containing 0.2% Triton-X 100 (PBT) at room temperature for thirty minutes, followed by three rinses of three minutes each in PBS. To help reduce auto-fluorescence in the tissue, the samples were incubated in 1% HCl in 70% ethanol at room temperature for twenty minutes, followed by three rinses of three minutes each in PBS. Blocking of non-specific binding sites was performed by incubating the slides in 1% Blocking Reagent (10.0 mg/ml BSA in PBS) at room temperature for twenty minutes. No washes were performed between the blocking step and the subsequent hybridization step.

Hybridization of Target Specific Antibodies to Biological Samples

Antibodies specific for a target are hybrized for example as follows:

A cocktail of anti-cytokeratin 18 (CK18) antibody (Calbiochem) diluted at 1:7000 and androgen receptor (AR) antibody (clone AR441, LabVision) diluted at 1:5 dilution was made in 1% Blocking Reagent. Approximately 100 µl of this antibody cocktail was applied to the tissue sample, and the antibodies and tissue samples were allowed to hybridize in a humid chamber at room temperature for one hour. Hybridization was followed by two rinses of six minutes each in PBT, one rinse of six minutes in PBS, and one rinse of three minutes in PBS.

Labeling of Hybridized Target Specific Antibodies

Hybridized target specific antibodies are flourescently labeled for example as follows:

A cocktail of Zenon Alexa Fluor 488 anti-Rabbit IgG Fab fragment and Zenon Alexa Fluor 568 anti-mouse IgG1 Fab fragment (Invitrogen, Carlsbad, Calif.) was made in 1% Blocking Reagent at twice the concentrations recommended by the manufacturer (1:50 dilution for each Fab fragment). Approximately 100 µl of this labeling cocktail was applied to the tissue samples, which were then incubated in a humid chamber at room temperature for 30 minutes. The labeling reaction was followed by two rinses of six minutes each in PBT, one rinse of six minutes in PBS, and one rinse of three minutes in PBS.

Multiplex Detection

Multiple targets in a single sample are detected using for example the following protocol. To identify 5 targets in a single prostate section using the following protocol: A cocktail of anti-racemase (AMACR; clone 13H4, Zeta Corporation) at a 1:50 dilution was made with undiluted antibody against high molecular weight cytokeratin+p63 (HMW CK+p63; BioCare Medical). Approximately 100 µl of this antibody cocktail was applied to the tissue sample, and the antibodies were allowed to bind in a humid chamber at room temperature for one hour. Incubation was followed by two rinses of six minutes each in PBT, one rinse of six minutes in PBS, and one rinse of three minutes in PBS.

For the labeling step, a cocktail of Zenon Alexa Fluor 488 anti-Rabbit, IgG Fab fragment Zenon Alexa Fluor 555 anti-mouse IgG1 Fab fragment, and Zenon Alexa Fluor 594 anti-mouse IgG2a Fab fragment was made in 1% Blocking Reagent at twice the concentrations recommended by the manufacturer (1:50 dilution for each Fab fragment). Approximately 100 µl of this labeling cocktail was applied to the tissue samples, and the tissue samples were incubated in a humid chamber at room temperature for 30 minutes. The labeling reaction was followed by two rinses of six minutes each in PBT, one rinse of six minutes in PBS, and one rinse of three minutes in PBS.

The tissue samples were then treated to a second round of antibody binding and labeling. A cocktail of anti-CK-18 at a 1:6000 dilution and anti-AR at a 1:5 dilution was made in 1% Blocking Reagent. Approximately 100 µl of this antibody cocktail was applied to the tissue sample, and the antibodies were allowed to bind in a humid chamber at room temperature for one hour. Hybridization was followed by two rinses of six minutes each in PBT, one rinse of six minutes in PBS, and one rinse of three minutes in PBS.

For the second labeling step, a cocktail of Zenon Alexa Fluor 647 anti-Rabbit IgG Fab fragment and Zenon Alexa Fluor 568 anti-mouse IgG1 Fab fragment was made in 1% Blocking Reagent at the concentration recommended by the manufacturer (1:100 dilution for each Fab fragment). Approximately 100 µl of this labeling cocktail was applied to the tissue samples, and the tissue samples were incubated and rinsed as described for the first labeling step.

Example 2

Multiplex Detection of Androgen Receptor, Cytokeratin and AMACR

Androgen Receptor (AR), Cytokeratin 18 and AMACR have been found to be important biomarkers for the evaluation of prostate cancerous tissue. The qualitative and quantitative distribution of these markers in formalin fixed, paraffin embedded tissue sections or Tissue Microarrays were detected as described below. Samples up to 16 years old were used in this study.

1.) Antigen Retrieval (in Reveal Solution, Citrate Buffer or Proteinase K)

For antigen retrieval, tissue sections or TMAs were heated in 1× Reveal Solution (BioCare Medical) in a decloaking chamber according to standard protocol and then allowed to cool for 15 minutes. Alternative methods of antigen retrieval include: 1) heating tissue sections or TMAs in 10 mM Citrate Buffer, pH6.0, for 15 minutes in a calibrated microwave followed by cooling for 15 minutes or 2) enzymatically digesting tissue sections or TMAs in a Proteinase K solution (commercially available from Fisher as a Ready-to-Use reagent for antigen retrieval for 12-15 minutes. After rinsing in distilled water for 15 minutes (this step is skipped for Proteinase K antigen retrieval), the slides were washed 3×5 minutes in Phosphate Buffered Saline (PBS).

2.) Autofluorescence Removal

Autofluorescence was reduced by incubating the slides in 1% HCl/70% EtOH for 10 minutes at room temperature. Slides were then rinsed 3×5 minutes in PBS.

3.) Tissue Permeabilization

Tissue was subsequently permeabilized in PBS containing 0.2% Triton X (PBT) for 30 minutes at room temperature.

4.) Blocking with Unspecific IgG

Non-specific binding of antibody or Fab fragment was be blocked by incubation with 0.5 µg/ul BSA in PBT for 20 minutes in a humidity chamber. Slides were subsequently rinsed in PBT for 5 minutes.

5.) Preparing Pre-Formed Complex for Cytokeratin 18 and Fab

Mouse monoclonal Cytokeratin 18 was incubated with Mouse specific Fab fragment labeled with Alexa 488 in order to prepare a pre-formed complex for 10 minutes at room temperature. After that unbound Fab was neutralized by adding a non-specific Mouse IgG in excess.

6.) Incubation of Untreated Primary Antibodies and Pre-Formed Complex on Tissue

Pre-formed Cytokeratin 18-Fab complex and untreated Rabbit polyclonal CD34 and Mouse monoclonal pTEN antibody were incubated on the tissue for 1 hour at room temperature in a humidity chamber.

7.) Removal of Unbound Antibody

Excess antibody was removed by washing the slides 2×10 minutes in PBT followed by 3×5 minutes in PBS.

8.) Incubation with Fluorescently Labeled Fab

Mouse and Rabbit specific Fab fragment labeled with Alexa 555 and Alexa 594 respectively were added to the slide and incubated for 30 minutes at room temperature in a humidity chamber.

9.) Removal of Unbound Fab

Unbound Fab fragment was removed by washing the slides 2×10 minutes in PBT followed by 3×5 minutes in PBS.

10.) Fixation Tissue was fixed in 10% formalin for 10 minutes. Slides were rinsed 2×5 minutes in PBS.

11.) Mounting

After adding 100 µl AntiFade solution containing nuclear counterstain, slides were coverslipped and prepared for imaging capture.

12.) Image Acquisition

Samples were placed on a 90i automated fluorescent microscope. Regions of interest were identified by moving the y-x axes of the microscope stage. Image exposure time was set to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis.

Example 3

Multiplex Detection of EGFR, Phospho-EGFR and Cytokeratin 18

The Epidermal Growth Factor Receptor (EGFR) and downstream signaling members have recently been shown to be over-expressed in certain tumor types. As a result another group of biomarkers under analysis are EGFR, phospho-EGFR and Cytokeratin 18. In order to measure the qualitative and quantitative distribution of these biomarkers in formalin fixed, paraffin embedded tissue sections or Tissue Microarrays were detected as follows:

Deparaffinization and re-hydration of tissue samples performed on the Discovery XT Automated Slide Processing Machine (Ventana Medical, Tuscan Ariz.).

1.) Antigen Retrieval (Proteinase K)

For antigen retrieval, tissue sections or TMAs were incubated in a Proteinase K solution (commercially available as a Ready-to-Use reagent for antigen retrieval) for 12-15 minutes. This was applied to slides in "pre-treatment 1" step of machine protocol using a user fillable dispenser (pretreatment 3).

2.) Tissue Permeabilization

Tissue samples were subsequently permeabilized in PBS containing 0.2% Triton X (PBT) for 28 minutes at room temperature, applied in "pre-treatment 2" step of protocol using a user fillable dispenser (enzyme 3).

3.) Auto Fluorescence Removal

Autofluorescence was reduced by incubating the slides in 1% HCl/70% EtOH for 16 minutes at room temperature, applied in pre-treatment step 3 of protocol using a fillable dispenser (pre-treatment 4).

4.) Blocking with Unspecific IgG

Non-specific binding of antibody or Fab fragments was blocked by incubation with 0.5 µg/ul BSA in PBT for 20 minutes in a humidity chamber. This was applied to slides in "Option" step of protocol using a user fillable dispenser (option 1).

5.) Incubation of Untreated Primary Antibodies

Mouse monoclonal EGFR and rabbit polyclonal phospho-EGFR antibody were diluted together into their respective working dilution and manual applied to slides during the manual titration step on the Discovery XT (Ventana Medical, Tuscan Ariz.). Discovery XT run was restarted for an hour incubation period 6.) Incubation with Fluorescently Labeled Fab Mouse and Rabbit specific Fab fragment labeled with Alexa 594 and Alexa 555 respectively were manually added to the slide and incubated for 30 minutes. Discovery XT run was restarted and allowed to run to completion.

7.) Removal of Unbound Antibody

After run was completed, slides were removed from Discovery XT, placed in slide rack and rinsed 2×6 minutes each in PBT at room temperature. Then slides were rinsed again 2×3 minutes in PBS.

7.) Incubation of Third Untreated Primary Antibody

Mouse monoclonal Cytokeratin 18 were diluted to its working dilution and added to slides for one hour incubation at room temperature.

8.) Incubation with Third Fluorescently Labeled Fab

Mouse specific Fab fragment labeled with Alexa 488 were added to the slide and incubated in the dark for 30 minutes at room temperature.

9.) Removal of Unbound Antibody

Excess antibody was removed by washing the slides 2×6 minutes in PBT followed by 3×3 minutes in PBS.

9.) Removal of Unbound Fab

Unbound Fab fragment was removed by washing the slides 2×10 minutes in PBT followed by 3×5 minutes in PBS.

10.) Fixation

Tissues were fixed in 10% formalin for 10 minutes. Slides were then be rinsed 2×5 minutes in PBS.

11.) Mounting

After adding 100 µl AntiFade solution containing nuclear counter stain, slides would be coverslipped and prepared for imaging capture.

12.) Image Acquisition

Samples were placed on a 90i automated fluorescent microscope. Regions of interest were identified by moving the y-x axes of the microscope stage. Image exposure time was set within the camera to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis.

Example 4

Multiplex Detection of VEGF, KDR, p-KDR and CD34

Angiogenesis is a critical process for tumor growth and metastasis. Vascular Endothelial Growth Factor (VEGF) and its receptor VEGFR-2 (KDR) along with CD34 have been found to be important biomarkers for evaluation of neovascularization and angiogenesis. In order to measure the qualitative and quantitative distribution of these biomarkers in formalin fixed, paraffin embedded tissue sections or Tissue Microarrays were detected as follows;

1.) Antigen Retrieval (in Reveal Solution)

For antigen retrieval, tissue sections or TMAs were heated in 1× Reveal Solution (BioCare Medical) in a decloaking chamber according to standard protocol and then allowed to cool for 15 minutes. Alternative methods of antigen retrieval include: 1) heating tissue sections or TMAs in 10 mM Citrate Buffer, pH6.0, for 15 minutes in a calibrated microwave followed by cooling for 15 minutes. After rinsing in distilled water for 15 minutes the slides would be washed 3×5 minutes in Phosphate Buffered Saline (PBS).

2.) Tissue Permeabilization

Tissue samples were subsequently permeabilized in PBS containing 0.2% Triton X (PBT) for 30 minutes at room temperature.

3.) Autofluorescence Removal

Autofluorescence was reduced by incubating the slides in 1% HCl/70% EtOH for 10 minutes at room temperature. Slides were then rinsed 3×5 minutes in PBS.

4.) Blocking with Unspecific IgG

Non-specific binding of antibody or Fab fragment was blocked by incubation with 0.5 µg/ul of BSA in PBT for 20 minutes in a humidity chamber. Slides were subsequently rinsed in PBT for 5 minutes.

5.) Incubation of Untreated Primary Antibodies

Mouse monoclonal VEGF and Rabbit polyclonal KDR were diluted together to working dilution and added to slides for one hour incubation in a humid chamber.

6.) Removal of Unbound Antibody

Excess antibody was removed by washing the slides 2×6 minutes in PBT followed by 2×3 minutes in PBS.

7.) Incubation with Fluorescently Labeled Fab

Mouse and Rabbit specific Fab fragment labeled with Alexa 488 and Alexa 555 respectively were added to the slide and incubated in the dark for 30 minutes.

8.) Removal of Unbound Antibody

Excess antibody was removed by washing the slides 2×10 minutes in PBT followed by 3×5 minutes in PBS.

9.) Incubation of Second Grouping of Untreated Primary Antibodies

Mouse monoclonal CD34 and Rabbit polyclonal phospho-KDR were diluted together to working dilution and added to slides for one hour incubation in a humid chamber.

10.) Removal of Unbound Antibody

Excess antibody was removed by washing the slides 2×6 minutes in PBT followed by 2×3 minutes in PBS 11.) Incubation with Fluorescently Labeled Fab Mouse and Rabbit specific Fab fragment labeled with Alexa 568 and Alexa 594 respectively were added to the slide and incubated in the dark for 30 minutes.

12.) Removal of Unbound Antibody

Excess antibody was removed by washing the slides 2×10 minutes in PBT followed by 3×5 minutes in PBS.

10.) Fixation

Tissue was fixed in 10% formalin for 10 minutes. Slides would then be rinsed 2×5 minutes in PBS.

11.) Mounting

After adding 100 µl AntiFade solution containing nuclear counter-stain the slides were cover slipped and prepared for imaging capture.

12.) Inage Acquisition

Samples were placed on a 90i automated fluorescent microscope. Regions of interest were identified by moving the y-x axes of the microscope stage. Image exposure time was set within the camera to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis.

Example 5

Multiplex Detection of Androgen Receptor, Cytokeratins, α-Methylacyl-CoARacemace, P63, CD34 and the NFKB Androgen receptor (AR, Mouse IgG1),Cytokeratin-18 (Rabbit IgG), Methylacyl-CoA Racemace (AMACR, Rabbit IgG), High Molecular Weight Cytokeratin (HMWCK, Mouse IgG1), P63 (Mouse IgG2a), CD34 (Mouse IgG1) and NFKB (Rabbit IgG) have been found to be important biomarkers for the evaluation of prostate cancerous tissue. The qualitative and quantitative distribution of these markers in formalin fixed, paraffin embedded tissue sections or Tissue Microarrays were detected as follows:

1.) Antigen Retrieval (in Reveal Solution, Citrate Buffer or Proteinase K)

For antigen retrieval, tissue sections or TMAs were heated in 1× Reveal Solution(BioCare Medical) in a decloaking chamber according to standard protocol and then allowed to cool for 15 minutes. Alternative methods of antigen retrieval include: 1) heating tissue sections or TMAs in 10 mM Citrate Buffer, pH6.0, for 15 minutes in a calibrated microwave followed by cooling for 15 minutes or 2) enzymatically digesting tissue sections or TMAs in a Proteinase K solution (commercially available as a Ready-to-Use reagent for antigen retrieval) for 12-15 minutes. After rinsing in distilled water for 15 (this step is skipped for Proteinase K antigen retrieval), the slides were washed 3×5 minutes in Phosphate Buffered Saline (PBS).

2.) Autofluorescence Removal

Autofluorescence was reduced by incubating the slides in 1% HCl/70% EtOH for 10 minutes at room temperature. Slides were then rinsed 3×5 minutes in PBS.

3.) Tissue Permeabilization

Tissue was subsequently permeabilized in PBS containing 0.2% Triton X (PBT) for 30 minutes at room temperature.

4.) Blocking with Unspecific IgG

Non-specific binding of antibody or Fab fragment was be blocked by incubation with 0.5 µg/µl BSA in PBT for 20 minutes in a humidity chamber. Slides were subsequently rinsed in PBT for 5 minutes.

5.) Preparing Pre-Formed Complex for High Molecular Weight Cytokeratin/p63 Cocktail and AMACR.

Mouse monoclonal High Molecular Weight Cytokeratin/P63 and rabbit polyclonal AMACR antibodies were titrated with the same non-specific binding antibody and incubated on tissue for 1 hr at room temperature in a humidity chamber.

6.) Removal of Unbound Antibody

Excess antibody was removed by washing the slides 2×5 minutes in PBT followed by 2 in PBS, 5 and 3 minutes respectively.

7.) Incubation with Fluorescently Labeled Fab

Mouse and Rabbit specific Fab fragment labeled with Alexa 488, Alexa 555 and Alexa 594 respectively were added to the slide and incubated for 30 minutes at room temperature in a humidity chamber.

8.) Removal of Unbound Fab

Unbound Fab fragment was removed by washing the slides 2×5 minutes in PBT followed by 2 in PBS 5 and 3 minutes respectively.

9.) Preparing Pre-Formed Complex for Cytokeratin 18 and Androgen Receptor

Mouse monoclonal Androgen Receptor (AR) and rabbit polyclonal Cytokeratin 18 antibodies were titrated with the same non-specific binding antibody and incubated on tissue for 1 hr at room temperature in a humidity chamber 10) Removal of Unbound Antibody Excess antibody was removed by washing the slides 2×5 minutes in PBT followed by 2 in PBS, 5 and 3 minutes respectively.

11) Incubation with Fluorescently Labeled Fab

Mouse and Rabbit specific Fab fragment labeled with Alexa 680 and Alexa 568 respectively were added to the slide and incubated for 30 minutes at room temperature in a humidity chamber.

12) Removal of Unbound Fab

Unbound Fab fragment was removed by washing the slides 2×5 minutes in PBT followed by 2 in PBS 5 and 3 minutes respectively.

13) Preparing for an Overnight Application of CD34 Antibody

Mouse monoclonal CD34 antibody was titrated with the same non-specific binding antibody and incubated overnight at 4 degrees in a closed humidity chamber.

14) Refrigerated Slides Retrieval

After removing slides from refrigerator, the slides were left at room temperature inside the closed humidity chamber for 1 hr.

15) Removal of Unbound Antibody

Excess antibody was removed by washing the slides 2×5 minutes in PBT followed by 2 in PBS, 5 and 3 minutes respectively.

16) Incubation with Fluorescently Labeled Fab

Mouse and Rabbit specific Fab fragment labeled with Alexa 647 was added to the slide and incubated for 30 minutes at room temperature in a humidity chamber.

17) Removal of Unbound Fab

Unbound Fab fragment was removed by washing the slides 2×5 minutes in PBT followed by 2 in PBS 5 and 3 minutes respectively.

18) Preparing for a Application of NFKB Antibody

Rabbit polyclonal NFKB was titrated with the same non-specific binding antibody and incubated on tissue for 1 hr at room temperature in a humidity chamber.

19) Removal of Unbound Antibody

Excess antibody was removed by washing the slides 2×5 minutes in PBT followed by 2 in PBS, 5 and 3 minutes respectively.

20) Incubation with Fluorescently Labeled Fab

Rabbit specific Fab fragment labeled with Alexa 660 was added to the slide and incubated for 30 minutes at room temperature in a humidity chamber.

21) Removal of Unbound Fab

Unbound Fab fragment was removed by washing the slides 2×5 minutes in PBT followed by 2 in PBS 5 and 3 minutes respectively.

22) Fixation

Tissue was fixed in 10% formalin for 10 minutes. Slides were rinsed 2×5 minutes in PBS.

23) Mounting

After adding 100 µl AntiFade solution containing nuclear counterstain, slides were coverslipped and prepared for imaging capture.

24) Image Acquisition

Samples were placed on a 90i automated fluorescent microscope. Regions of interest were identified by moving the y-x axes of the microscope stage. Image exposure time was set to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis.

Example 6

Multiplex Detection of Cytokeratin 18, AMACR Racemase, Androgen Receptor, High Molecular Weight Keratin and P63 in Prostate Tissue The standard MultiPlex assay was used to detect of 5 markers including CK18 (Cytokeratin 18), AMACR (Racemase), AR (Androgen Receptor), HMWK (High Molecular Weight Keratin), p63 (basal cells) and DAPI for identifying nuclei on formalin fixed paraffin embedded prostate tissue sections.

One H&E (Hematoxylin and Eosin) and five unstained paraffin sections from 6 individual patients were studied. The H&E sections were evaluated by two pathologists for overall quality and tumor content. Utilizing a standard multiplex protocol described in EXAMPLES 1-4 above, a quintplex assay was performed which included an assessment of CK18, AMACR, AR, HMWK, and p63 on a single slide from each patient. A DAPI stain was utilized to identify nuclei. Positive and negative control prostate tissue samples from a tissue microarray were run in parallel. Three images were acquired from selected regions, processed and subsequently analyzed. Data was exported and quantitative metrics were associated to individual images.

All six patient samples contained variable degrees of tumor with associated benign and PIN elements. The overall quality of the sectioned material was acceptable and all samples were assayed with the quintplex M-Plex. Triplicate images were acquired from each prostate tissue section. Individual gray scale tiff images were processed using spectral imaging software and then analyzed with the immunofluorescent algorithms to generate quantitative features. Some 90 individual features were generated using the image analysis scripts. The features represent various phenotypic characteristics of cellular compartments and their association with a specific biomarker. For example, the antigens/biomarker in question are queried based on their cellular distribution as well as overall mean and standard deviation with respect to their intensity (amount) which is derived from pixel (px) levels. The individual scripts for the quintplex assay have been previously normalized in order to account for variations with respect to tissue thickness, variability in penetration of fixative and quality/access of antigen. As a means of illustration two of the six patients will be discussed in the following sections.

Figure 10A:
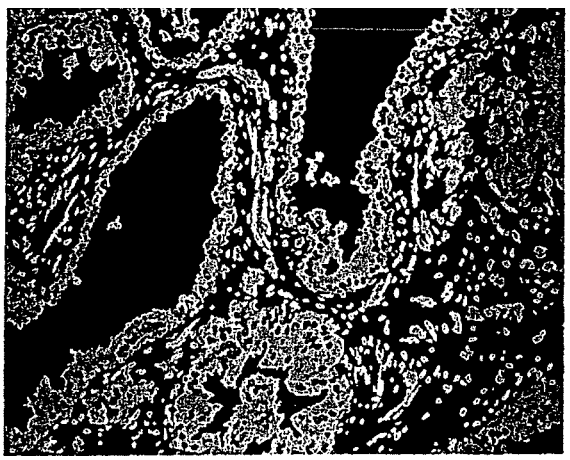
FIG. 10 are photographs showing a single region of interest in patient ID 4752-1.
Figure 10B:
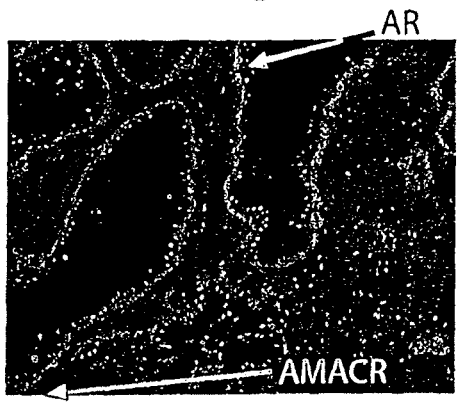
Figure 10C:
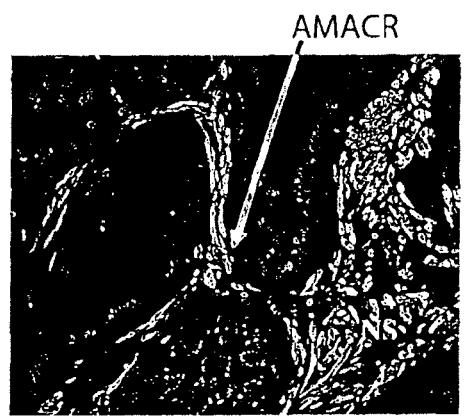
Figure 11A:
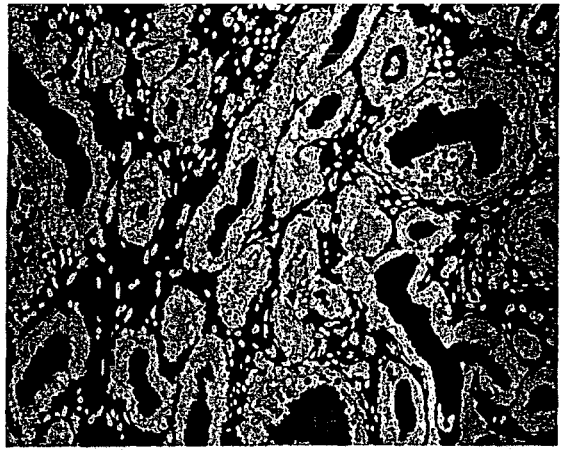
FIG. 11 are photographs showing a single region of interest in patient ID 4754-2.
Figure 11B:
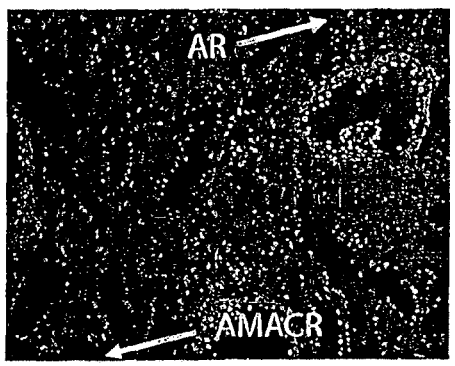
Figure 11C:
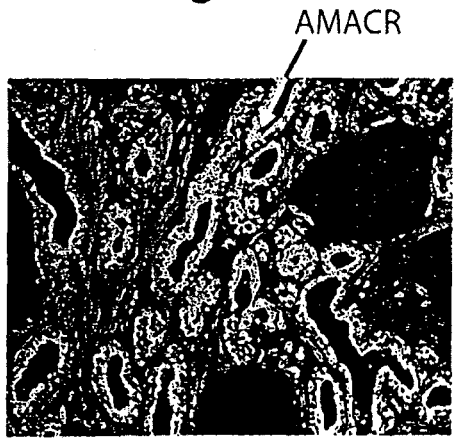

The acquired images from the test tissue samples were evaluated based on a review of the segmented (FIG. 10A; note color key for specific classification) and gray scale images for AR (FIG. 10B) and AMACR (FIG. 10C; NS refers to non-specific binding of AMACR to stroma).

For patient ID 4754-2, the average intensity of AR present within epithelial cells that are AMACR positive was 0.45 vs. 0.43 for AMACR negative cells illustrating that even though there are more AMACR positive glands present, the average intensity of AR within the AMACR positive group is low when compared to the AMACR negative cell population. In addition, the average amount of AR intensity in the stroma was 3.09, the relative area of epithelial nuclei that are AR positive and AMACR positive was 0.20, the relative area of all epithelial nuclei that are AR positive was 0.61 and finally the overall intensity of AMACR was 324,849 pixels. The imaging feature results delineate subtle differences between selected regions of interest, cell types and their associated antigens; allowing these differences to be quantified and then included within predictive models or evaluated individually with respect to outcome/response. For model building, specific features are evaluated with respect to an outcome and their level of accuracy is assessed by a confidence interval. Features are initially screened within the context of a training set and then validated in an external cohort for confirmation.

This study confirms the ability to apply the quintplex multiplex assay across external formalin fixed, paraffin embedded tissue sections. The assay was successful across all 6 patient samples r, with completion of image acquisition, processing and generation of quantitative features which assess the levels and intensity of the Androgen Receptor and AMACR within individual tissue samples.

In addition the quintplex was performed on formalin fixed and paraffin embedded LNCaP and PC3 known from numerous publications to exhibit both high (LNCaP) and low (PC3) levels of AR expression, respectively. The association of a quantitative value to AR content within these cell lines is the first step towards understanding AR modulation and the impact on down stream effector molecules as evidenced by the reduction in AMACR within the PC3 cells. These in vitro approaches are the first step towards examining AR response to a drug (i.e. Androgen Deprivation Therapy (ADT), Histone Deacetylase Inhibitors, HDAC)) and can easily be extended to patient clinical samples including needle aspirates, biopsy specimens to determine drug (on target) response, titration and efficacy.

Example 7

Multiplex Detection of CD4, CD8, CD25, CD69 and CD86

The object of this study was to develop the necessary immunofluorescent Multiplex (M-Plex) assays for the proposed CD4, CD8, CD25, CD69 and CD86 plus CK18. The CK18 is retained within the two final m-plex assays in order to identify tissue compartments (epithelial vs. stroma) for quantitative script development. This process entails the identification of appropriate commercial sources for all reagents, assay development including titration, Alex Fluorochrome selection and analysis using both non-prostate control tissue samples. The goal was to complete the development of both the simplex and M-plex assays for each of the markers and acquire images which can subsequently be utilized for quantitative script development.

Several commercial sources for the specific antigens/antibodies that were included in the development of the M-plex assays (see Table 1).

TABLE 1

| Antibody | Vendor | Catalog # | Clone | Isotype | Dilution |
| --- | --- | --- | --- | --- | --- |
| CK-18 (R) | CalBiochem | AP1021 | Synthetic peptide | RIgG | 1:1250 |
| CD4 | Vector Labs | VP-C318 | 1F6 | MIgG1 | 1:10 |
| CD8 | Vector Labs | VP-C325 | 1A5 | MIgG1 | 1:10 |
| CD25 | LabVision | MS-203-P1 | 4C9 | MIgG1 | 1:200 |
| CD69 | BioLegend | 310902 | FN50 | MIgG1 | 1:10 |
| CD86 | GeneTex | 74653 | BU63 | MIgG1 | 1:10 |

Utilizing a series of control tissue samples including tonsil, lymph node and spleen each of the individual antibodies were titrated and assessed by the pathologists for background, and specificity/sensitivity of signal based on cellular distribution, and localization. The antibodies are each tested individually in a simplex IF format and then rapidly advanced to the m-plex assay according to the methods outlined below.

Quantitative Immunofluorescence

De-paraffinization and re-hydration of tissue samples were performed per standard operating procedures on a Leica 5020 auto-stainer. Antigen retrieval was performed by boiling the slides in a microwave oven for 7.0 minutes in 1× Reveal Solution. The slides were allowed to cool for 20 minutes at room temperature and then were washed twice for three minutes in PBS.

All tissue samples were stained at room temperature on a BioCare Medical Nemesis 7200 automated slide stainer. The tissue samples underwent the following pre-hybridization treatment steps. To help permeate the cellular structures of the tissue, the samples were incubated in PBT (PBS+0.2% Triton-X 100) for thirty minutes, followed by one rinse of three minutes in TBS. To help reduce auto-fluorescence in the tissue, the samples were incubated in 1% HCl in 70% EtOH for twenty minutes, followed by one rinse of three minutes in TBS. Blocking of non-specific binding sites was performed by incubating the slides in Blocking Reagent (PBT containing 1.0 mg/ml BSA) for twenty minutes. No washes were performed between the blocking step and the subsequent hybridization step.

For the final triplex multiplex I, a 1:200 dilution of CD25 (4C9) was made in Blocking Reagent. For the final duplex multiplex, a 1:10 dilution of CD8 (1A5) was made in Blocking Reagent. Approximately 400.0 μl of the appropriate antibody was applied to the tissue sample, and the antibodies and tissue samples were allowed to hybridize for one hour. Hybridization was followed by one rinse of three minutes in TBS.

The triplex multiplex was labeled with Zenon Alexa Fluor Mouse 532, diluted in Blocking Reagent at twice the concentrations recommended by the manufacturer (1:50 dilution). The duplex multiplex was labeled with Zenon Alexa Fluor Mouse 594, diluted as described. Approximately 400.0 µl of the appropriate label was applied to the tissue samples, and the tissue samples were incubated for thirty minutes. The labeling reaction was followed by one rinse of three minute in TBS.

The tissue samples for both multiplexes were then treated to a second round of hybridization and labeling. For the triplex, a 1:10 dilution of CD69 (FN50) was made in Blocking Reagent. For the duplex, a cocktail of Cytokeratin 18 (CK-18) at a 1:1,000 dilution and CD86 (BU63) at a 1:10 dilution was made in Blocking Reagent. Approximately 400.0 µl of the appropriate antibody/cocktail was applied to the tissue sample, and the antibodies and tissue samples were allowed to hybridize for one hour. Hybridization was followed by one rinse of three minutes in TBS.

For the second labeling step, triplex was labeled with Zenon Alexa Fluor Mouse 555, diluted as described. The duplex was labeled with a cocktail of Zenon Alexa Fluor Mouse 555 and Zenon Alex Fluor Rabbit 647, diluted as described. Approximately 400.0 µl of the appropriate label(s) was applied to the tissue samples, and the tissue samples were incubated for thirty minutes. The labeling reaction was followed by one rinse of three minutes in TBS.

The tissue samples for the triplex were then treated to a third round of hybridization and labeling. The duplex was advanced to the fixation step described below. For the triplex, a cocktail of Cytokeratin 18 (CK-18) at a 1:1,000 dilution and CD4 (1F6) at a 1:10 dilution was made in Blocking Reagent. Approximately 400.0 µl of the antibody cocktail was applied to the tissue sample, and the antibodies and tissue samples were allowed to hybridize for one hour. Hybridization was followed by one rinse of three minutes in TBS.

For the third labeling, the triplex was labeled with a cocktail of Zenon Alexa Fluor Mouse 594 and Zenon Alex Fluor Rabbit 647, diluted as described. Approximately 400.0 µl of the label cocktail was applied to the tissue samples, and the tissue samples were incubated for thirty minutes. The labeling reaction was followed by two rinses of three minutes in TBS.

A fixation step was performed by incubating the samples in 10% formalin for 10 minutes, followed by two rinses of three minutes each in TBS. The slides were then removed from the BioCare Medical Nemesis 7200 automated slide stainer.

Molecular Probe's SlowFade Gold antifade reagent with DAPI (approximately 25.0 µl) was applied to the samples, which were then cover slipped. Samples were stored at −20° C. until analysis could be performed.

Figure 12:
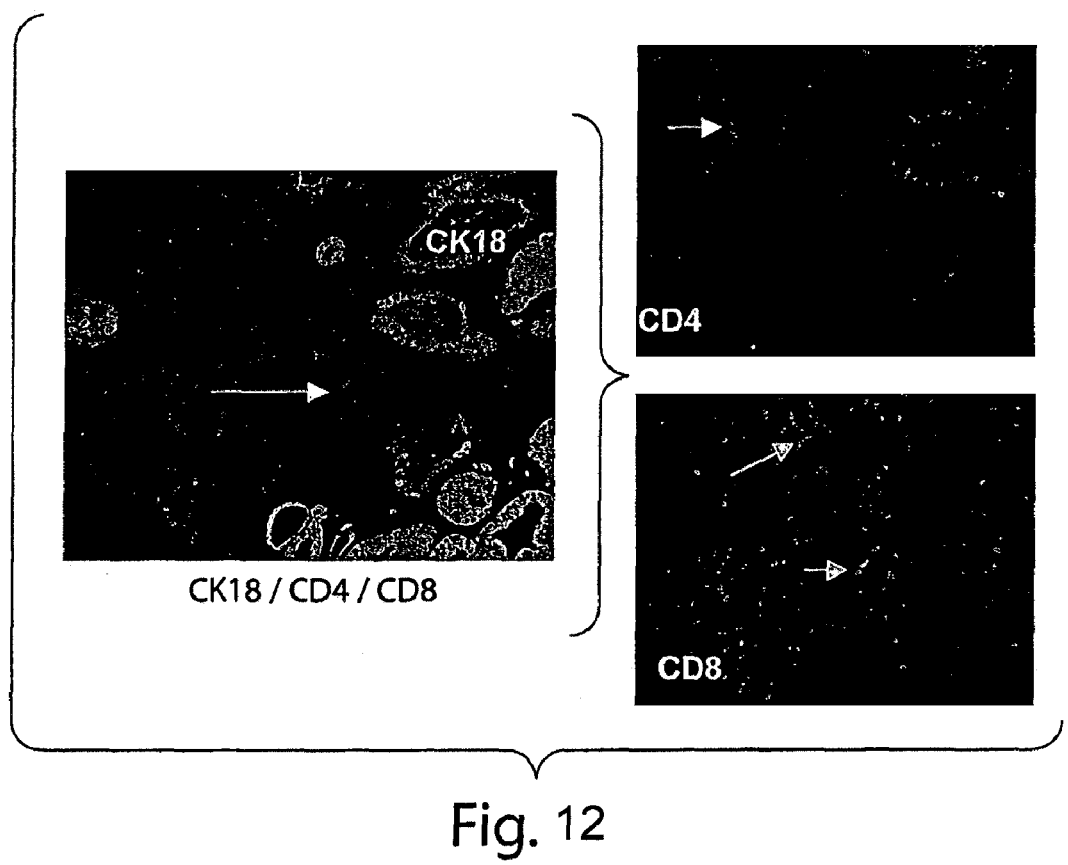
FIG. 12 are photographs showing duplex M-plex with CD4 and CD8. Note stromal localization adjacent to CK18 positive epithelial cells.

The five antibodies were divided between two M-plex assays due to the common isotype of available reagents. The antibodies were first developed and analyzed in simplex immunofluorescent assay using lymphoid tissue specimens (i.e. spleen, tonsil, lymph node) where it was anticipated that all markers would be present. The results from the simplex assay were successful in that each of the markers identified subsets of lymphocytes which matched cellular compartment (i.e. cellular membrane) and were identified within intervening follicles and or germinal centers. The original simplex experiments were then grouped into two M-plex formats that were applied across similar control tissues as well as in-house prostate tissue samples where lymphocytic infiltrates were identified by H&E evaluation. Examples of the data derived from these original M-plex assays are illustrated in FIGS. 12A and 12B. As demonstrated, two M-plex assays were developed. M-plex I is a duplex that contained CD4 and CD8 (+CK18) while a second M-plex II was a triplex that contained CD25, 69 and 86 (+CK18).

Figure 13:
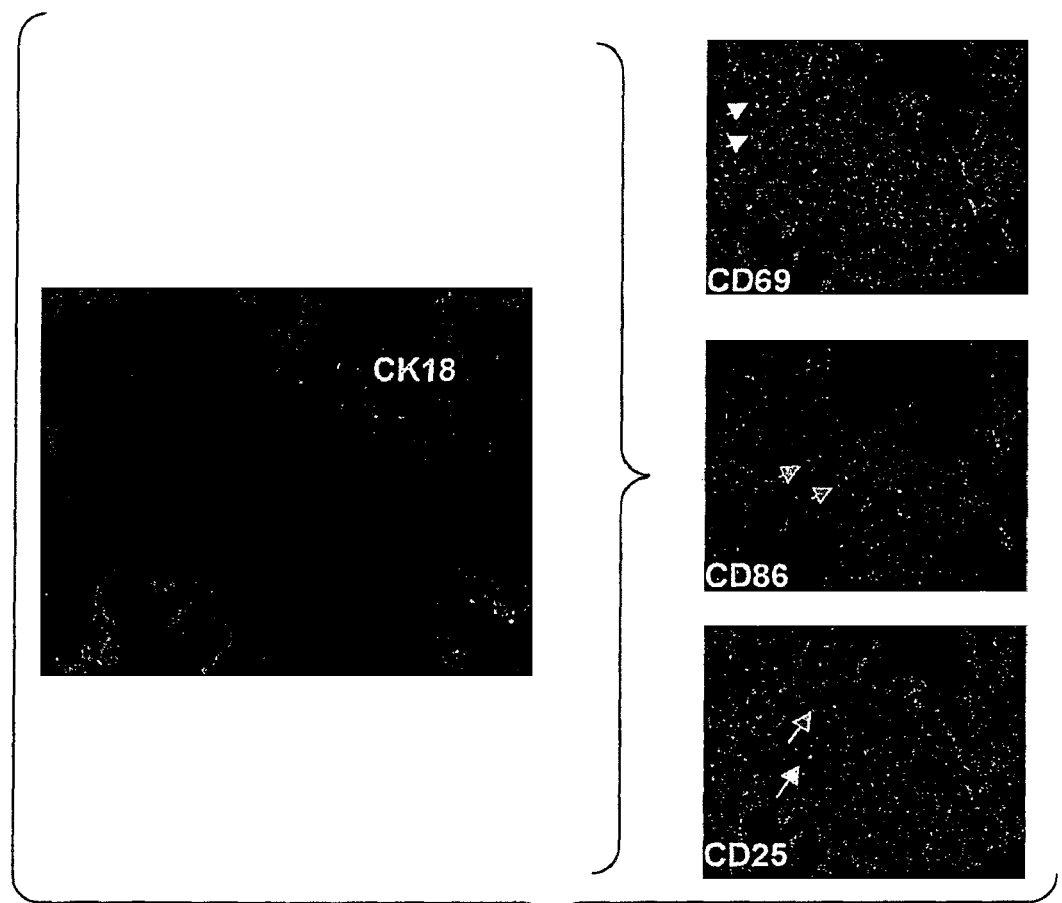
FIG. 13 are photographs showing triplex M-plex with CD25, 69 and 86. Note stromal localization adjacent to CK18 positive epithelial cells FIG. 14 are photographs showing duplex M-plex on Spleen illustrating the distribution and cellular localization of CD8 and 86. Note the abundance of CD8 lymphocytes present within the spleen along with the expected mature activated B cells as evidenced by the CD86 staining. (AF=Auto fluorescence).
Figure 14:
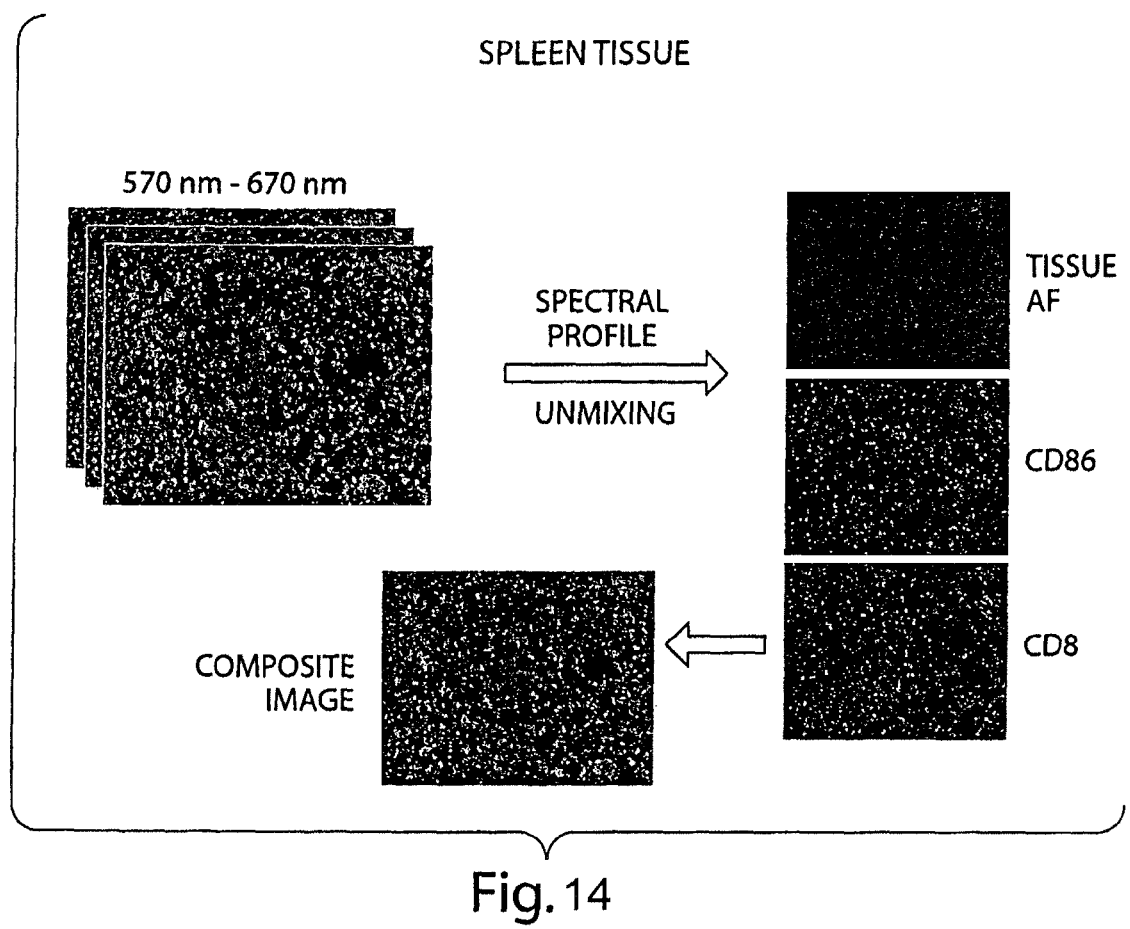
Figure 15:
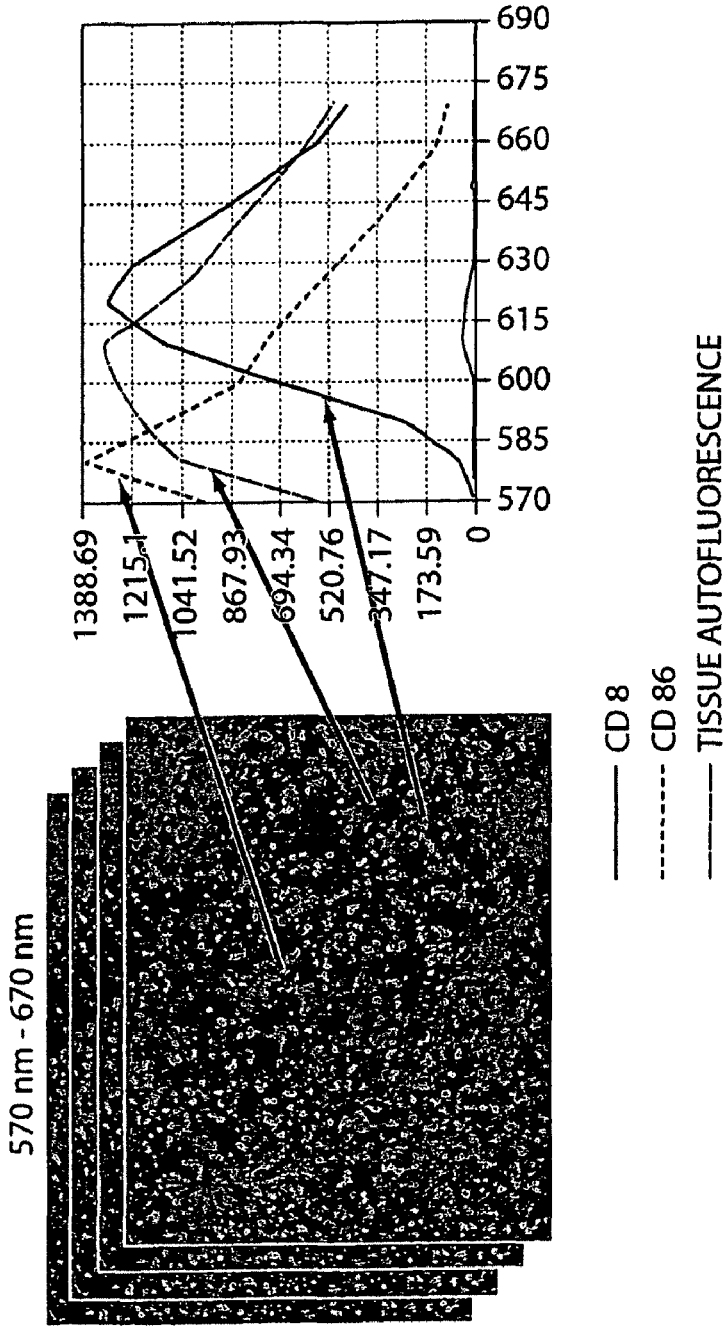
FIG. 15 is a schematic illustrating spectral detection of CD8 an CD86 in spleen tissue.
Figure 16:
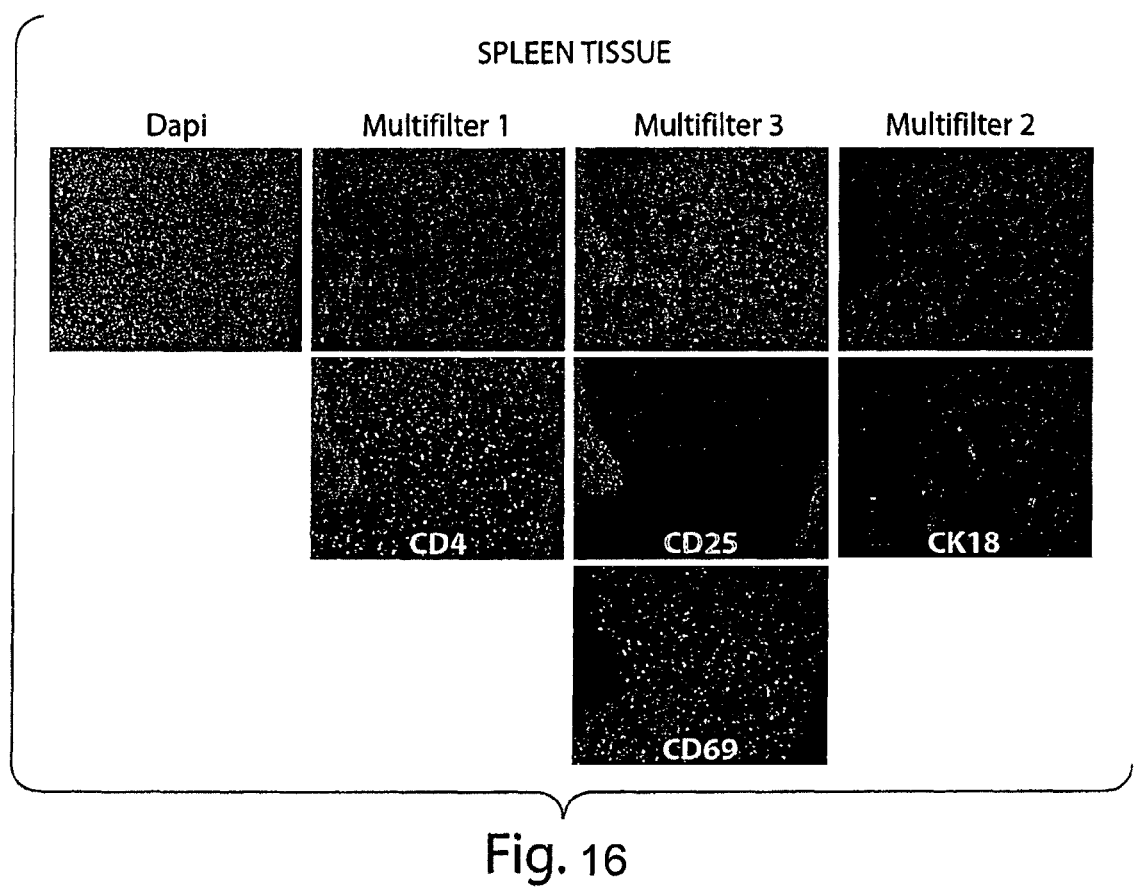
FIG. 16 are photographs showing triplex M-plex on Spleen illustrating the distribution and cellular localization of CD4, 25 and 69. Note the abundance of CD4 lymphocytes within the spleen as expected with varying amounts of CD25 and CD69.
Figure 17:
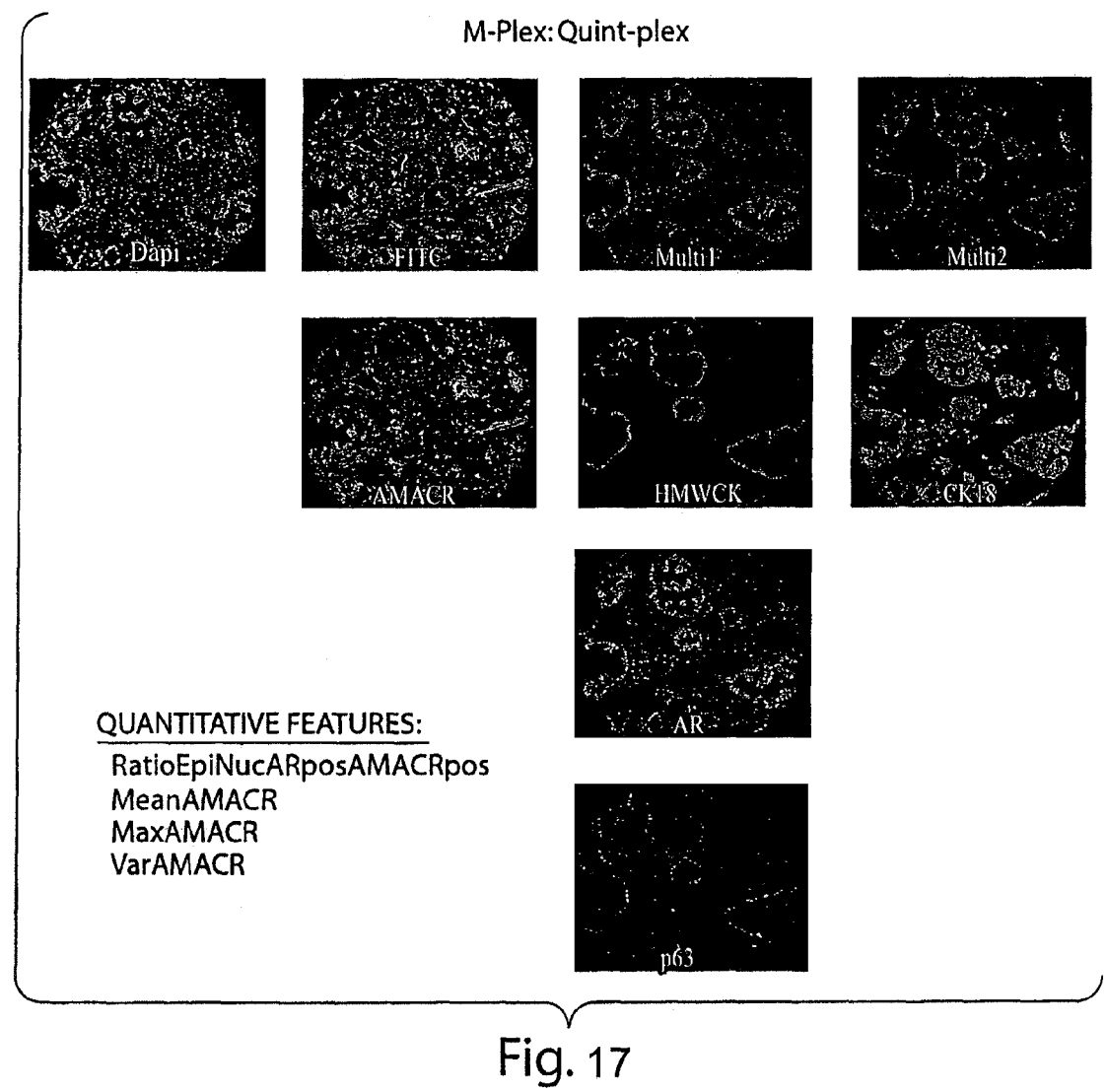
FIG. 17 are photographs showing a quintplex.
Figure 18:
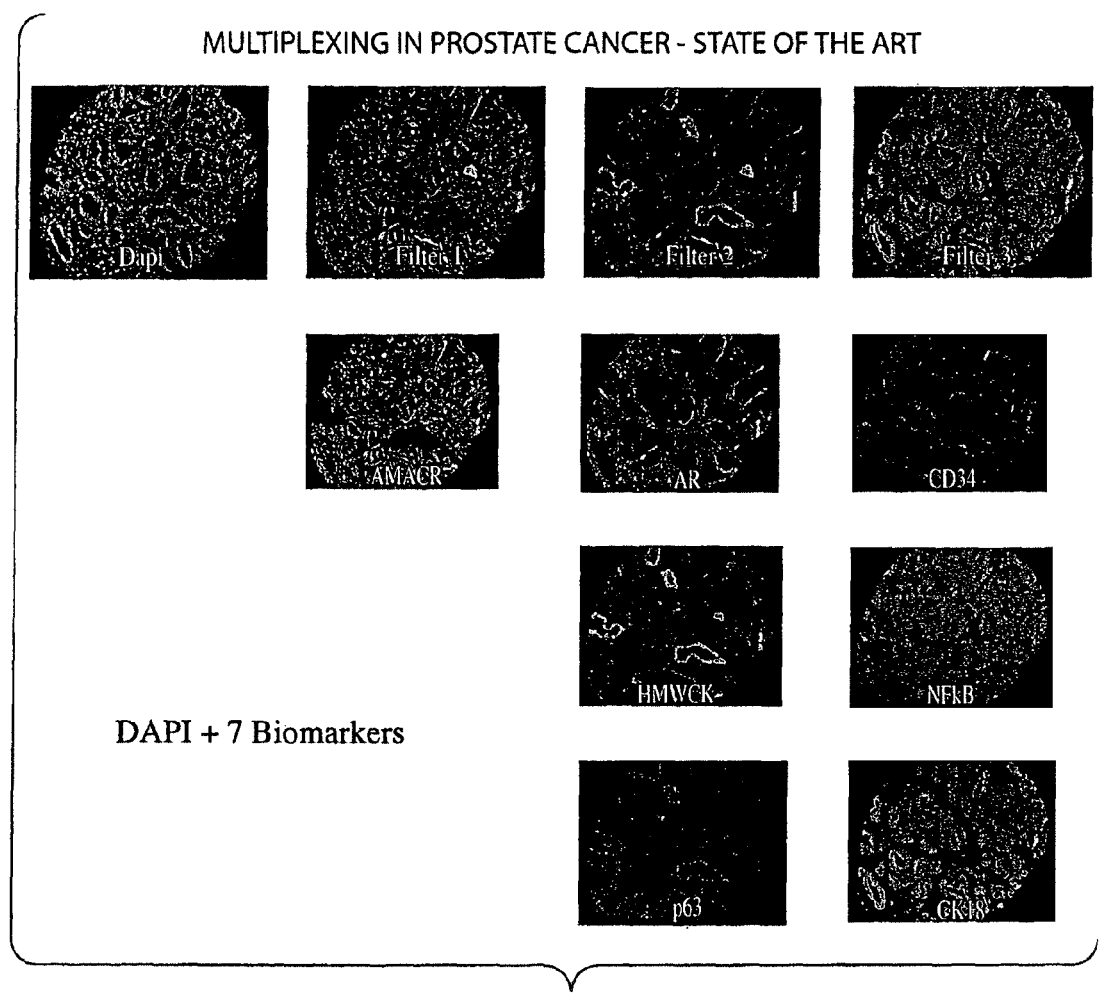
FIG. 18 are photographs showing a 7-plex in prostate tissue.
Figure 19:
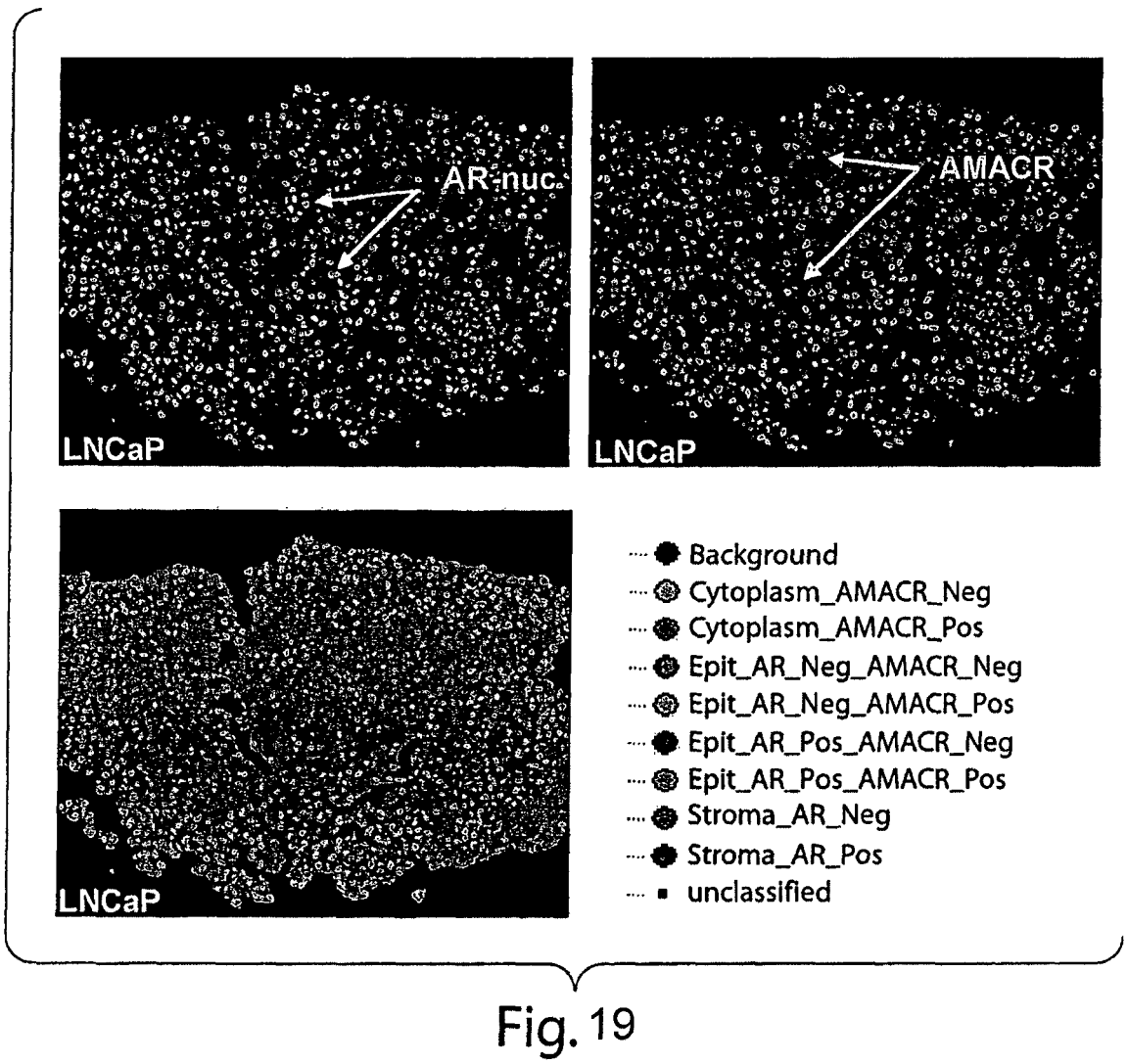
FIG. 19 are photographs showing a quintplex on cell lines.
Figure 20:
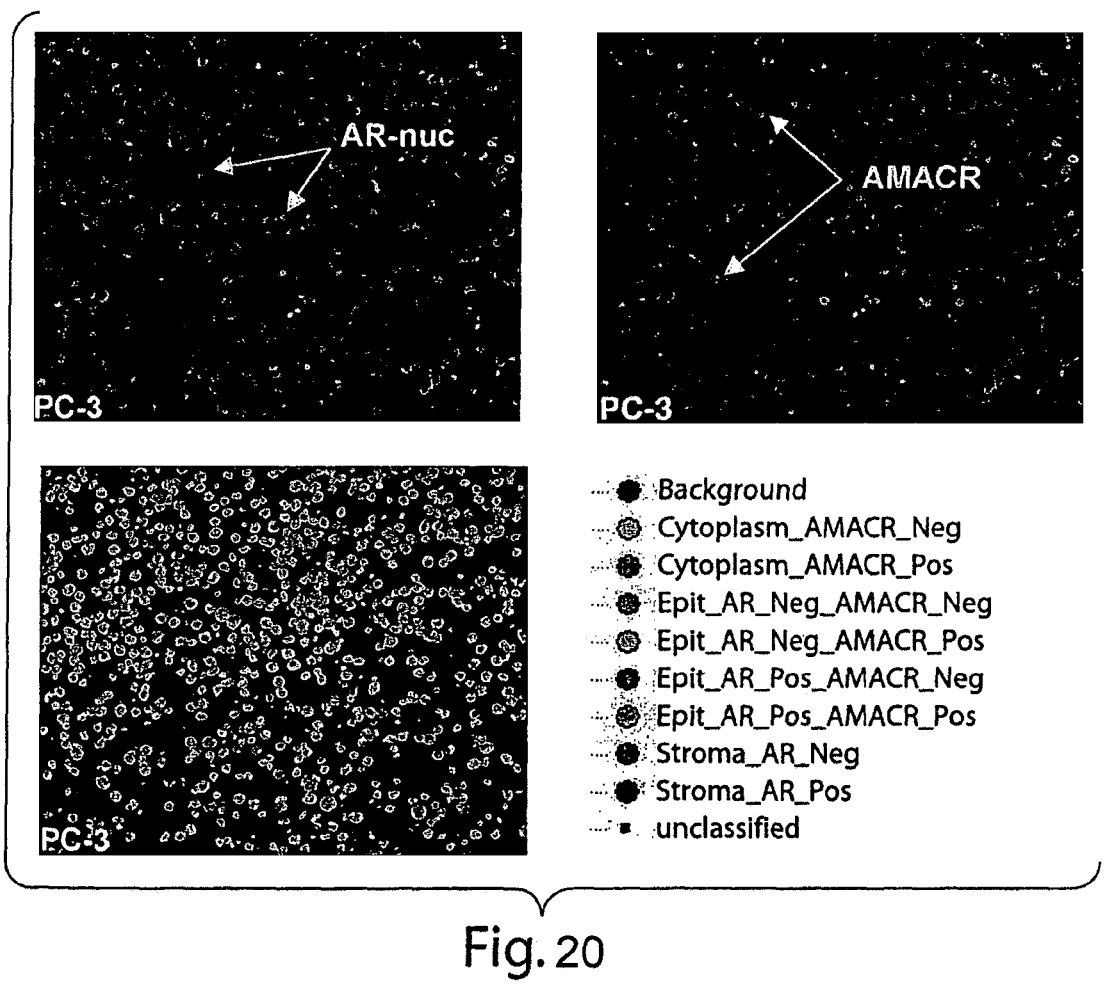
FIG. 20 are photographs showing a quintplex on cell lines.

Subsequent to the development of the above M-plex formats, two additional M-plex combinations were generated to evaluate selected subsets of T cells within given tissue sections (e.g. activated T cells—CD4+CD69+ and mixed T cells: CD4+ and CD25+. The new M-plex formats consisted of a duplex which contained CD8 and 86 and a triplex which contained CD4, 25 and 69. These new M-plex assays were tested on spleen and tonsil tissue samples and are illustrated in FIGS. 13A and 13B. These are the m-plex formats that will be applied on the patient treated prostatectomy samples when they arrive at Aureon.

For each M-plex experiment, a spectral profile identifying the individual Alexa Fluor emission profile is evaluated for signal quality, differentiation from other profiles, intensity, and initial quality assessment for quantification for script development (signal/noise). The Alexa Fluorochromes are selected based on their spectral profiles in order to preserve the purity of the signal with the least amount of overlap. As illustrated in FIG. 13B. the spectral profiles for the duplex M-plex identify individual antigens/antibodies as well as tissue auto fluorescence. A similar analysis was also performed for the triplex m-plex.

Through an evaluation of localization within lymphoid follicles and individual lymphoid tissue types the current antibodies within these M-plex formats were able to selectively identify populations of lymphocytes. The gray scale images (as outlined in the figures) will be utilized for algorithm and script development in order to successfully quantify these antigens in tissue sections.

The development of both IF simplex and IF M-plex assays for the evaluation of the 5 antibodies/antigens—CD4, CD8, CD25, CD69 and CD86 has been successfully completed. These 5 antibodies have been coupled (in specific M-plex formats) in order to maximize over-lay for script development such that subsets of activated lymphocytic cell populations.

Example 8

Peptide Microarry for Measuring the Dynamic Range and Quantitation of Target Detection Peptides are short amino acid sequences (typically 10 to 30 residues) that are often used as immunogens for antibody production. Because they can be synthesized in vitro, purified peptides they can be produced in large quantities. Typically, peptide microarrays consist of peptides covalently attached to a glass surface. If an antibody recognizes a specific peptide sequence, a peptide array can thus be utilized to measure the dynamic range (the range between the lowest and the highest concentration of target) that can be detected with said method. Additionally, since a given peptide concentration on the microarray is linked to a specific fluorescent intensity, the unknown target concentration can be quantitatively assessed.

A peptide microarray was designed that contains a peptide which is specifically recognized by NeoMarkers (Lab Vision Corp.) NM-MS443 anti Androgen Receptor antibody (Peptide sequence: STEDTAEYSPFKGGYTK (SEQ ID NO: 1)). Additionally, the microarray contained a positive control peptide (Sequence: NFLMDNA(pY)FCEADAKKK (SEQ ID NO: 2)) that is specifically detected by an anti phospho-Tyrosin antibody (Sigma) and a negative control peptide which is not related to any known protein (Sequence: SFYGATGESYDPTTKEK (SEQ ID NO: 3)). All peptides were spotted in triplicates in following concentrations: 100, 500, 250, 125, 62.5, 31.25, 15.63, 7.81, 3.91 and 1.95 micro molar. The microarray was manufactured by JPT Peptide Technologies, Germany.

Peptide microarray staining was performed as follows:

1.) Attach Chamber to Peptide Microarray Slide

Each adhesive frame was sandwiched between a thin and a thick polyester sheet (while the thin sheet covers the adhesive frame completely, the thick sheet has a central part remove). The thick polyester was removed, leaving the blue frame attached to the thin sheet. Next the blue adhesive frame on the thin polyester sheet was placed onto the glass slide while avoiding contact with the peptide displaying surface. The blue frame was firmly pressed down without trapping air under the adhesive. The second thin polyester sheet was then removed from the top of the adhesive blue frame. The blue frame alone remained attached to the slide.

2.) Prepare Assay Solution with Primary

A volume of 1.0 µg of the mouse monoclonal AR antibody (NeoMarkers, Lab Vision Corp.) was adjusted to 20 µl of 1×PBS buffer in an eppendorf tube. To undergo primary antibody labeling with a fluorophore, 5 µl of Zenon 555 Alexa Flour Ms IgG1 was then added. The solution was pipetted up and down to mix and incubated for 10 minutes. As a control, 7 µg/ml FITC-labeled phospho-Tyrosine antibody (Sigma) was diluted in tube along with additional AR antibody to its working dilution for a final assay solution volume of 330 µl. The solution was vortexed to ensure mixing, and starting at one end of the adhesive frame the complete volume was pipetted unto the entire slide surface.

3.) Incubation

The peptide microarray was then incubated for 4 hours at 4° C. in a light protected humid chamber.

4.) Remove Incubation Chamber

Assay solution was decanted and the incubation chamber is carefully removed by holding the slide with one hand and gently pulling up one edge of the adhesive blue frame. The blue frame was lifted off the edges of slide carefully to avoid any remaining adhesive which would disturb the following washes.

5.) Removal of Unbound Antibody

Excess antibody was removed by washing the slide 5 times for 5 minutes with double distilled filtered water. The slide was then washed with 5 times for 5 minutes in methanol.

6.) Mounting

After the slide was air dried (free of dust particles) 100 µl AntiFade solution containing nuclear counter-stain was added and then cover slipped and prepared for imaging acquisition.

7.) Image Acquisition

Peptide Arrays were placed on a 90i automated fluorescent microscope. Spots were located by moving the y-x axes of the microscope stage. Image exposure time was set within the camera to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis. Finally, brightness values were plotted against peptide concentrations in order to visualize the dynamic range of target detection.

Some antigens are expressed only in minor amounts in the tissue of interest. In order to achieve detection of those targets, said method can be modified in the following way: After adding the primary antibody and removal of unbound antibody by a washing step, a species specific secondary antibody is added. For example, if the primary antibody is Mouse IgG, a Goat anti-Mouse antibody would be added in the second step. After the species specific antibody is removed (in this case the Goat anti-Mouse IgG), the secondary antibody would be detected with fluorescently labeled Fab. Since more than one Goat anti-Mouse antibody can bind to each Mouse IgG, more fluorescent Fab fragments will bind to the detection complex.

Example 9

Signal Amplification

Some antigens are expressed only in minor amounts in the tissue of interest. In order to achieve detection of those targets, the simplex and multiplex methods of the invention are modified in the following way: After adding the primary antibody and removal of unbound antibody by a washing step, a species specific secondary antibody is added. For example, if the primary antibody is Mouse IgG, a Goat anti-Mouse antibody would be added in the second step. After the species specific antibody is removed (in this case the Goat anti-Mouse IgG), the secondary antibody would be detected with fluorescently labeled Fab. Since more than one Goat anti-Mouse antibody can bind to each Mouse IgG, more fluorescent Fab fragments will bind to the detection complex.

Androgen Receptor (AR) has been found to be important biomarkers for the evaluation of prostate cancerous tissue. In order to increase the signal intensity obtained to measure the qualitative and quantitative distribution of this markers in formalin fixed, paraffin embedded tissue sections or Tissue the follow method was used were detected as follows:

1) Antigen Retrieval (in Reveal Solution) For antigen retrieval, tissue sections or TMAs were heated to boiling in 1× Reveal Solution (BioCare Medical) (10 cc) in a calibrated high power microwave oven for 7½ minutes and then allowed to cool for 20 minutes. After cooling, the slides were washed 3×5 minutes in Phosphate Buffered Saline (PBS).

2) Tissue Permeabilization

Tissue samples were subsequently permeabilized in PBS containing 0.2% Triton-X (PBT) for 30 minutes at room temperature.

3) Autofluorescence Removal

Autofluorescence was reduced by incubating the slides in 1% HCl/70% EtOH for 20 minutes at room temperature. Slides were then rinsed 3×5 minutes in PBS.

4) Blocking with Unspecific IgG

Non-specific binding of antibody or Fab fragment was blocked by incubation with 0.5 µg/ul BSA in PBT for 20 minutes in a humidity chamber. Slides were not rinsed prior to the addition of the primary antibody to the tissue sample.

5) Incubation of Untreated Primary Antibody on Tissue

Untreated Mouse monoclonal Androgen receptor antibody was incubated on the tissue for 1 hour at room temperature in a humidity chamber.

6) Removal of Unbound Antibody

Excess antibody was removed by washing the slides 2×10 minutes in PBT followed by 3×5 minutes in PBS.

7) Incubation with Goat Anti-Mouse IgG Secondary Antibody

Goat anti-mouse IgG was diluted in PBT and was incubated on the tissue for 20 minutes at room temperature in a humidity chamber.

8) Removal of Unbound Goat Anti-Mouse IgG

Excess antibody was removed by washing the slides 2×10 minutes in PBT followed by 3×5 minutes in PBS.

9) Incubation with Fluorescently Labeled Fab

Mouse specific Fab fragment labeled with Alexa 568 was added to the slide and incubated for 30 minutes at room temperature in a humidity chamber.

9) Removal of Unbound Fab

Unbound Fab fragment was removed by washing the slides 2×10 minutes in PBT followed by 3×5 minutes in PBS.

10) Fixation

Tissue was fixed in 10% formalin for 10 minutes. Slides were rinsed 2×5 minutes in PBS.

11) Mounting

After adding 100 μl AntiFade solution containing nuclear counterstain, slides were coverslipped and prepared for imaging acquisition.

12) Image Acquisition

Samples were placed on a 90i automated fluorescent microscope. Regions of interest were identified by moving the y-x axes of the microscope stage. Image exposure time was set within the camera to the highest possible brightness level without causing overexposure. Images were acquired with the Nikon 1200DXM CCD camera or comparable system (alternatively a spectral imaging camera might be used for advanced spectral separation of fluorescent dyes). Images were saved in tiff format and subjected to quantitative image analysis.

Example 10

Detection Reagents

The following list of antibodies have been successfully immunofluorescently labeled with the secondary labeling technique employing Zenon™ Alexa Fluor labeling of antibodies after the antibody has been hybridized to the tissue source. These are suitable antibodies to use in the simplex/multiplex methods of the invention.

TABLE 2

| ANTIBODY | COMPANY SOURCE | CATALOG # | ISOTYPE |
|---|---|---|---|
| Actin | Zymed Laboratories | 18-0106 | Mouse IgG2a |
| phospho-AKT | Abcam Incorporated | ab4802 | Rabbit IgG |
| AMACR | Zeta Corporation | Z2001 | Rabbit IgG |
| Androgen Receptor | NeoMarkers (Lab Vision Corp.) | NM-MS443 | Mouse IgG1 |
| Bax | Abcam Incorporated | ab7977 | Rabbit IgG |
| Bcl-2 | DakoCytomation | M0887 | Mouse IgG1 |
| Caspase 3 (activated) | Chemicon International, Inc. | ab3623 | Rabbit IgG |
| CD-34 | DakoCytomation | M7165 | Mouse IgG1 |
| CD-45 | DakoCytomation | M0855 | Mouse IgG1 |
| Cytokeratin-14 | Vector Laboratories | VP-C410 | Mouse IgG1 |
| Cytokeratin-18 | Vector Laboratories | VP-C414 | Mouse IgG1 |
| Cyclin D1 | BioCare Medicals | CP236B | Rabbit IgG |
| Cyclin E | Vector Laboratories | VP-C396 | Mouse IgG2a |
| e-cadherin | Ventana Medical Systems, Inc. | 760-2830 | Mouse IgG1 |
| EGFR | DakoCytomation | K1492 | Mouse IgG |
| pEGFR (Y1068) | Abcam Incorporated | ab5644 | Rabbit IgG |
| EMA | DakoCytomation | M0613 | Mouse IgG1 |
| phospho-ERK | Cell Signaling Technologies | ab4376 | Rabbit IgG |
| EZH2 | Zymed Laboratories | 18-7395 | Rabbit IgG |
| Her-2/Neu | DakoCytomation | A0485 | Rabbit IgG |
| KDR | Upstate | 07-158 | Rabbit IgG |
| phopspho-KDR | Upstate | 07-374 | Rabbit IgG |
| Ki-67 | Ventana Medical Systems, Inc. | 290-2910 | Mouse IgG1 |
| phospho-mTOR | Cell Signaling Technologies | ab2971 | Rabbit IgG |
| p27 | Vector Laboratories | VP-P951 | Mouse IgG2a |
| p53 | DakoCytomation | M7001 | Mouse IgG2b |
| p70 S6 Kinase | Cell Signaling Technologies | ab9430 | Rabbit IgG |
| PI3 Kinase | Cell Signaling Technologies | ab3821 | Rabbit IgG |
| PSA | Ventana Medical Systems, Inc. | 760-2506 | Rabbit IgG |
| PSMA | Anogen | Y-PSMA-1 | Mouse IgG2a |
| pTEN | NeoMarkers (Lab Vision Corp.) | NM-MS1797 | Mouse IgG1 |
| α-tubulin | Zymed Laboratories | 18-0092 | Mouse IgG1 |
| VEGF | Abcam Incorporated | ab1316 | Mouse IgG1 |

We claim:

1. A method of detecting whether each of at least three targets are present or absent in a biological sample comprising the steps of:
   (a) performing antigen retrieval on the biological sample, wherein said antigen retrieval comprises the steps:
      i. de-paraffinize and re-hydrate biological sample and
      ii. boil in antigen retrieval buffer;
   (b) performing autofluorescence reduction on the biological sample prior to step (a), or step (c), wherein said autofluorescence reduction comprises incubating said biological sample in a solution comprising 1% hydrochloric acid and 70% ethanol;
   (c) contacting the biological sample with (1) a first antibody specific for a first target, (2) a first labeling reagent wherein said first labeling reagent comprises an antibody binding moiety for said first antibody and a first fluorescent detection moiety, (3) a second antibody specific for a second target, (4) a second labeling reagent comprising an antibody binding moiety for said second antibody and a second fluorescent detection moiety, (5) a third antibody specific for a third target, and (6) a third labeling reagent comprising an antibody binding moiety for said third antibody and a third fluorescent detection moiety; and
   (d) detecting a presence or an absence of each of said first, second and third labeling reagents, respectively, in said biological sample whereby the presence of said first, second or third labeling reagents indicates the presence of said first, second or third targets, respectively, in said biological sample and the absence of said first, second or third labeling reagents indicates the absence of said first, second or third targets, respectively, in said biological sample,
   wherein said biological sample is paraffin-embedded human tissue, and wherein prior to step (d) said sample is washed one or more times to remove unbound labeling reagent.

2. The method of claim 1, further comprising the step of washing said biological sample prior to step (c).

3. The method of claim 1, wherein the antibody binding moiety for at least one of said first, second or third labeling reagents is a monovalent antibody fragment or a non-antibody protein.

4. The method of claim 3, wherein said monovalent antibody fragment is a Fab or Fab' fragment.

5. The method of claim 4, wherein said Fab or Fab' fragment is selected from the group consisting of an anti-Fc antibody fragment, an anti-kappa light chain antibody fragment, an anti-lambda light chain antibody fragment, and a single chain antibody fragment.

6. The method of claim 3, wherein said monovalent antibody fragment is derived from a monoclonal antibody or a polyclonal antibody.

7. The method of claim 3, wherein said nonantibody protein is selected from the group consisting of a protein G, a protein A, a protein L, and a lectin.

8. The method of claim 1, wherein at least one of said targets is a nuclear protein or an oncoprotein.

9. The method of claim 1, wherein the presence of at least one of said targets is indicative of tumor cell heterogeneity.

10. The method of claim 1 wherein at least one of said targets is an androgen receptor, a cytokeratin 18, or a PTEN protein.

11. The method of claim 1, wherein at least one of said antibodies is a monoclonal antibody.

12. The method of claim 1, wherein step (c) comprises forming a complex between at least one of said labeling reagents and said antibodies within a tissue section.

13. The method of claim 1, wherein said biological sample is substantially free of nucleic acids before said detecting step.

14. The method of claim 1, further comprising the step of tissue permeabilization prior to step (c).

15. The method of claim 1, further comprising contacting said biological sample with an antibody specific for a fourth target and a fourth fluorescent labeling reagent.

16. The method of claim 15, further comprising contacting said biological sample with an antibody specific for a fifth target and a fifth fluorescent labeling reagent.

17. The method of claim 16, further comprising contacting said biological sample with an antibody specific for a sixth target and a sixth fluorescent labeling reagent.

18. The method of claim 17, further comprising contacting said biological sample with an antibody specific for a seventh target and a seventh fluorescent labeling reagent.

19. The method of claim 1, wherein at least one of said targets is selected from the group consisting of Androgen Receptor, Ki67, Cyclin D1, P-PKC zeta, Alpha-methylacyl-CoA racemase (AMACR), Epidermal Growth Factor Receptor (EGFR), PI3K, NFkB, P-KDR, vascular endothelial growth factor (VEGF), CD34, pAKT and Caspase 3a.

20. The method of claim 1, wherein said biological sample is at least 10 years old.

21. A method of detecting whether each of at least three targets are present or absent in a biological sample comprising the steps of:
(a) performing antigen retrieval on the biological sample, wherein said antigen retrieval comprises the steps:
  i. de-paraffinize and re-hydrate biological sample and
  ii. boil in antigen retrieval buffer;
(b) performing autofluorescence reduction on the biological sample prior to step (a), or step (c), wherein said autofluorescence reduction comprises incubating said biological sample in a solution comprising 1% hydrochloric acid and 70% ethanol;
(c) contacting said biological sample with
  i. a first complex, comprising an first antibody specific for a first target and a first labeling reagent wherein said labeling reagent comprises an antibody binding moiety specific for said first antibody and a first fluorescent detection moiety;
  ii. a second antibody specific for a second target and a second labeling reagent comprising an antibody binding moiety specific for said second antibody and a second fluorescent detection moiety; and
  iii. a third antibody specific for a third target, and a third labeling reagent comprising an antibody binding moiety for said third antibody and a third fluorescent detection moiety;
(d) detecting a presence or an absence of each of said first, second and third labeling reagents, respectively, in said biological sample whereby the presence of said first, second or third labeling reagent indicates the presence of said first, second or third target, respectively in said biological sample and the absence of said first, second or third labeling reagent indicates the absence of said first, second or third target, respectively, in said biological sample,
wherein said biological sample is paraffin-embedded human tissue, and wherein prior to step (d) said sample is washed one or more times to remove unbound labeling reagent.

22. The method of claim 21, further comprising the step of washing said biological sample prior to step (c).

23. The method of claim 21, further comprising the step of tissue permeabilization prior to step (c).

24. The method of claim 21, wherein the antibody binding moiety at least one of said first, second or third labeling reagents is a monovalent antibody fragment or a non-antibody protein.

25. The method of claim 24, wherein said monovalent antibody fragment is a Fab or Fab' fragment.

26. The method of claim 24, wherein said Fab or Fab' fragment is selected from the group consisting of an anti-Fc antibody fragment, an anti-kappa light chain antibody fragment, an anti-lambda light chain antibody fragment, and a single chain antibody fragment.

27. The method of claim 24, wherein said monovalent antibody fragment is derived from a monoclonal antibody or a polyclonal antibody.

28. The method of claim 24, wherein said nonantibody protein is selected from the group consisting of a protein G, a protein A, a protein L, and a lectin.

29. The method of claim 21, wherein said biological sample is at least 10 years old.

30. The method of claim 21, wherein at least one of said targets is a nuclear antigen or an oncoprotein.

31. The method of claim 21, wherein the presence of at least one of said targets is indicative of tumor cell heterogeneity.

32. The method of claim 21, wherein at least one of said targets is an androgen receptor, a cytokeratin 18, or a PTEN protein.

33. The method of claim 21, wherein at least one of said targets is selected from the group consisting of Androgen Receptor, Ki67, Cyclin D1, P-PKC zeta, Alpha-methylacyl-CoA racemase (AMACR), Epidermal Growth Factor Receptor EGFR), PI3K, NFkB, P-KDR, vascular endothelial growth factor (VEGF), CD34, pAKT and Caspase 3a.

34. The method of claim 21, wherein at least one of said first, second and/or third antibodies is a monoclonal antibody.

35. The method of claim 21, wherein step (c) comprises forming a complex between at least one of said labeling reagents and said antibodies within a tissue section.

36. The method of claim 21, further comprising contacting said biological sample with an antibody specific for a fourth target and a fourth fluorescent labeling reagent.

37. The method of claim 36, further comprising contacting said biological sample with an antibody specific for a fifth target and a fifth fluorescent labeling reagent.

38. The method of claim 37, further comprising contacting said biological sample with an antibody specific for a sixth target and a sixth fluorescent labeling reagent.

39. The method of claim 38, further comprising contacting said biological sample with an antibody specific for a seventh target and a seventh fluorescent labeling reagent.

* * * * *